United States Patent
Liu et al.

(10) Patent No.: US 11,406,605 B2
(45) Date of Patent: Aug. 9, 2022

(54) THERAPEUTIC COMPOSITIONS FOR TREATING PANCREATIC CANCER

(71) Applicant: Golden Biotechnology Corporation, Jersey City, NJ (US)

(72) Inventors: Sheng-Yung Liu, New Taipei (TW); Chih-Ming Chen, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 0 days.

(21) Appl. No.: 16/157,557

(22) Filed: Oct. 11, 2018

(65) Prior Publication Data

US 2019/0183813 A1 Jun. 20, 2019

Related U.S. Application Data

(60) Provisional application No. 62/608,549, filed on Dec. 20, 2017.

(51) Int. Cl.
| | |
|---|---|
| *A61K 31/122* | (2006.01) |
| *A61P 35/00* | (2006.01) |
| *A61K 31/337* | (2006.01) |
| *A61K 31/506* | (2006.01) |
| *A61K 31/7068* | (2006.01) |
| *A61K 45/06* | (2006.01) |

(52) U.S. Cl.
CPC .......... *A61K 31/122* (2013.01); *A61K 31/337* (2013.01); *A61K 31/506* (2013.01); *A61K 31/7068* (2013.01); *A61K 45/06* (2013.01); *A61P 35/00* (2018.01)

(58) Field of Classification Search
CPC ................ A61K 31/122; A61K 31/337; A61K 31/506; A61K 31/7068; A61K 45/06; A61P 35/00
See application file for complete search history.

(56) References Cited

U.S. PATENT DOCUMENTS

| | | | |
|---|---|---|---|
| 2011/0009494 A1* | 1/2011 | Liu ...................... | A61K 31/122 514/690 |
| 2015/0018296 A1* | 1/2015 | Liu ...................... | A61K 31/122 514/43 |

FOREIGN PATENT DOCUMENTS

CN 101343247 A * 1/2009

OTHER PUBLICATIONS

English transation of CN 101343247A, pp. 1-18, publ. 2009 (Year: 2009).*
Kim et al., Cancer Chemother. Pharmacol., publ. 2009, vol. 63, pp. 529-533 (Year: 2009).*
Tao et al., Mar. Drugs, publ. 2010, vol. 8, pp. 1094-1105 (Year: 2010).*
Stella, J. Pharm. Sci., publ. 2010, vol. 99(12), pp. 4755-4765 (Year: 2010).*
Kotteas et al., J. Cancer Res. Clin. Oncol., publ. 2016, vol. 142, pp. 1795-1805 (Year: 2016).*

* cited by examiner

*Primary Examiner* — Sarah Pihonak

(57) ABSTRACT

The present invention is directed to therapeutic compositions for treating pancreatic cancer comprising a cyclohexnone compound and one or more anti-cancer agents.

7 Claims, 19 Drawing Sheets

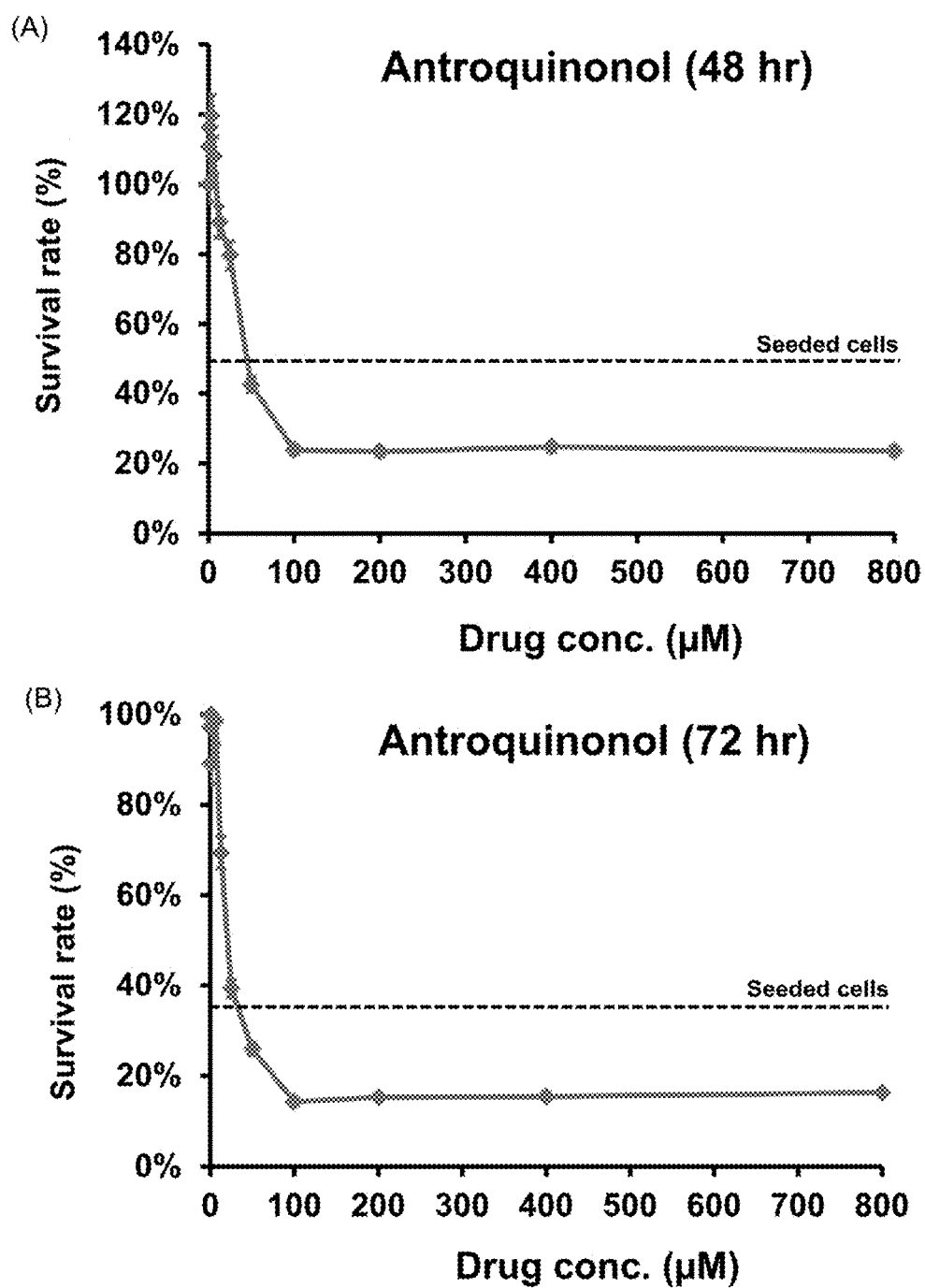
FIG. 1A-B

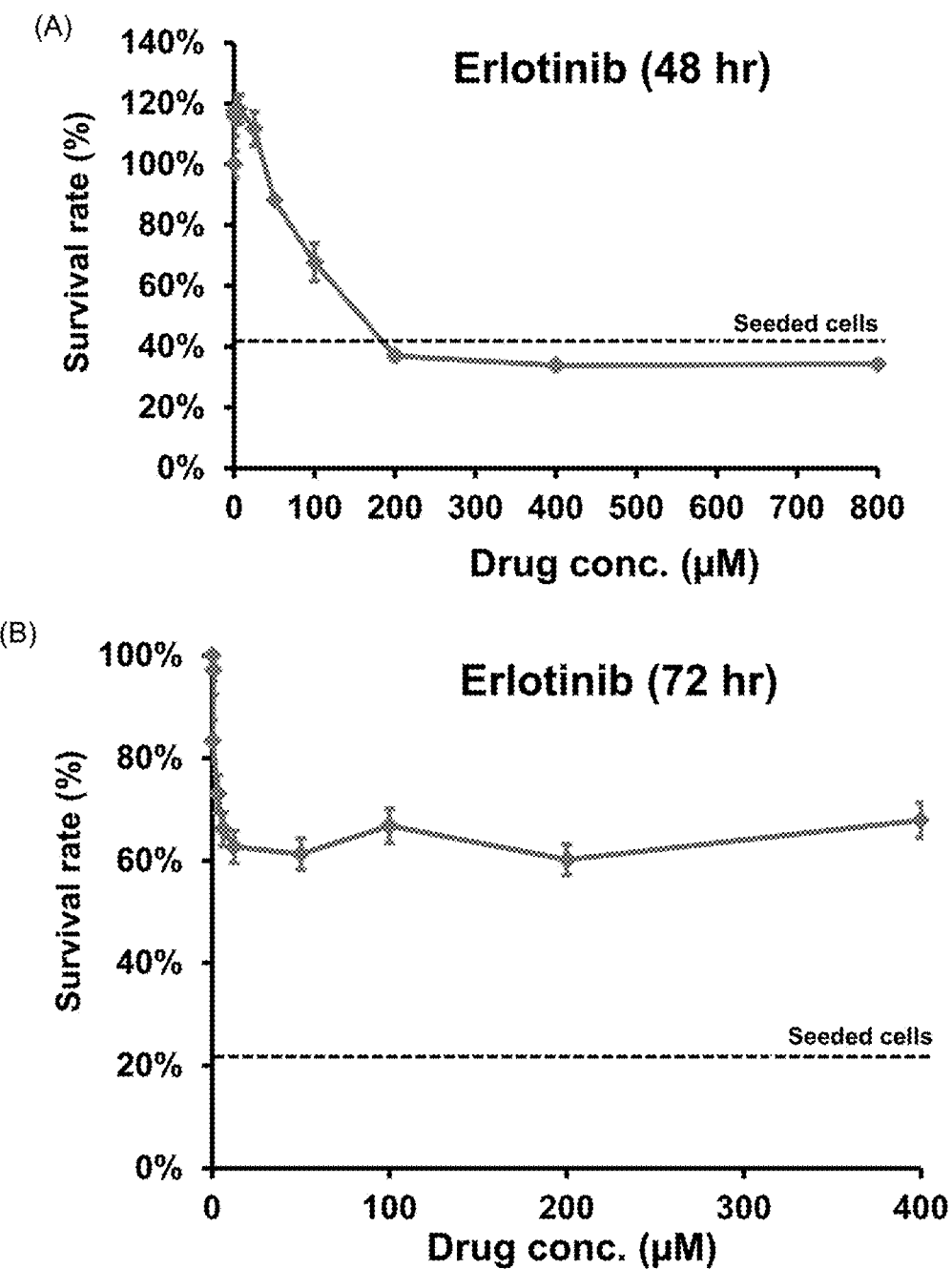
FIG. 2A-B

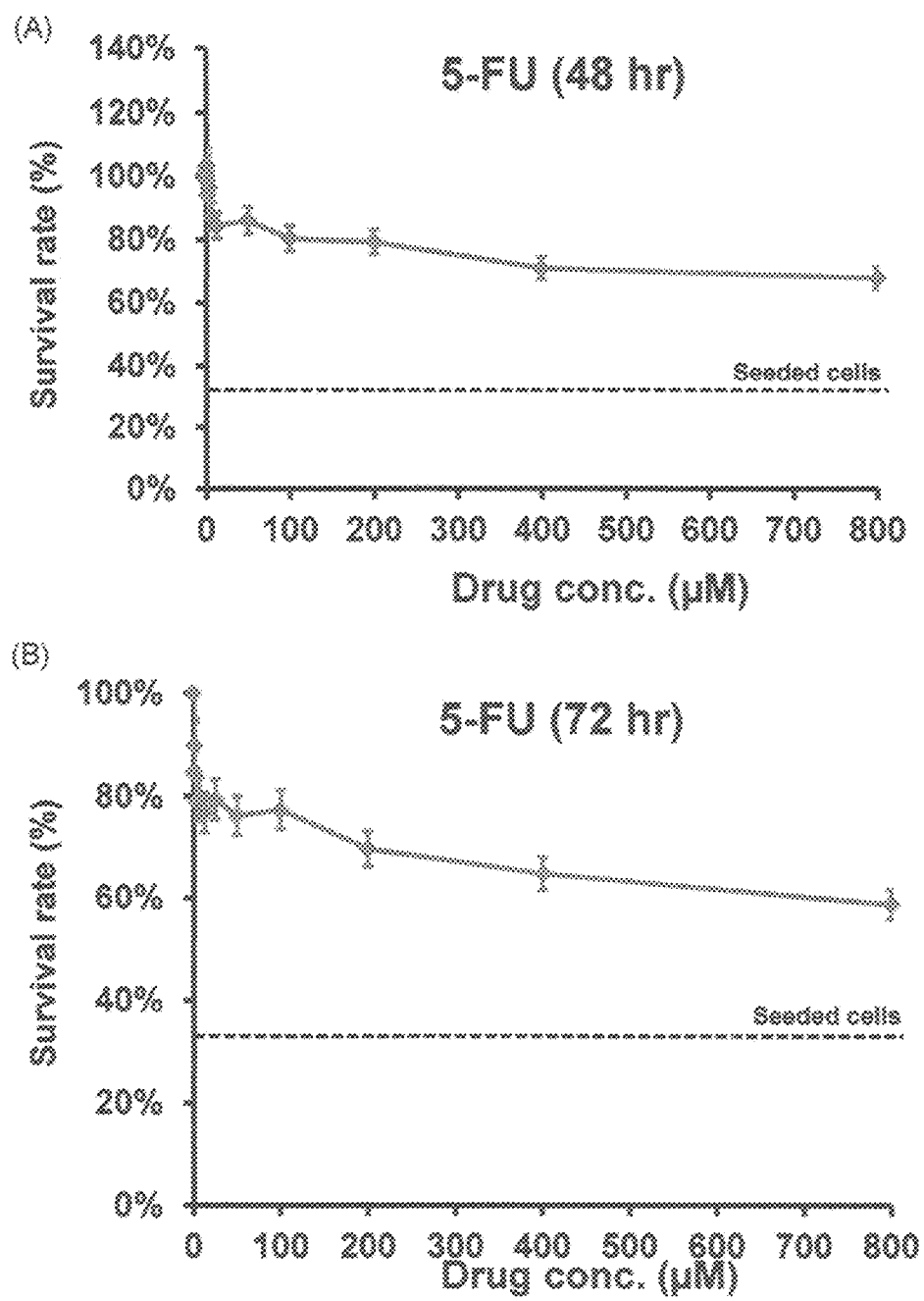
FIG. 3A-B

FIG. 4A-B
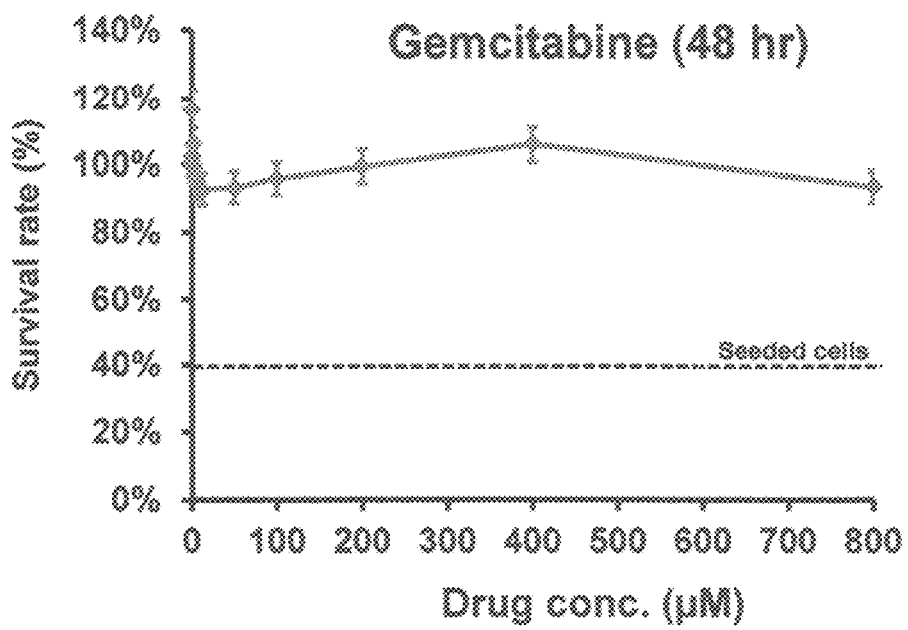
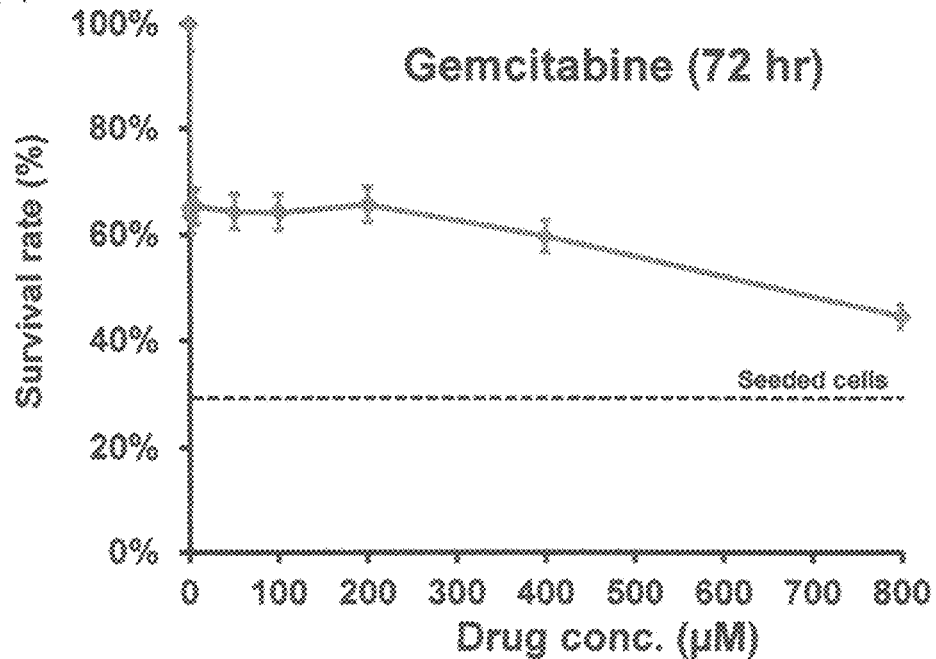

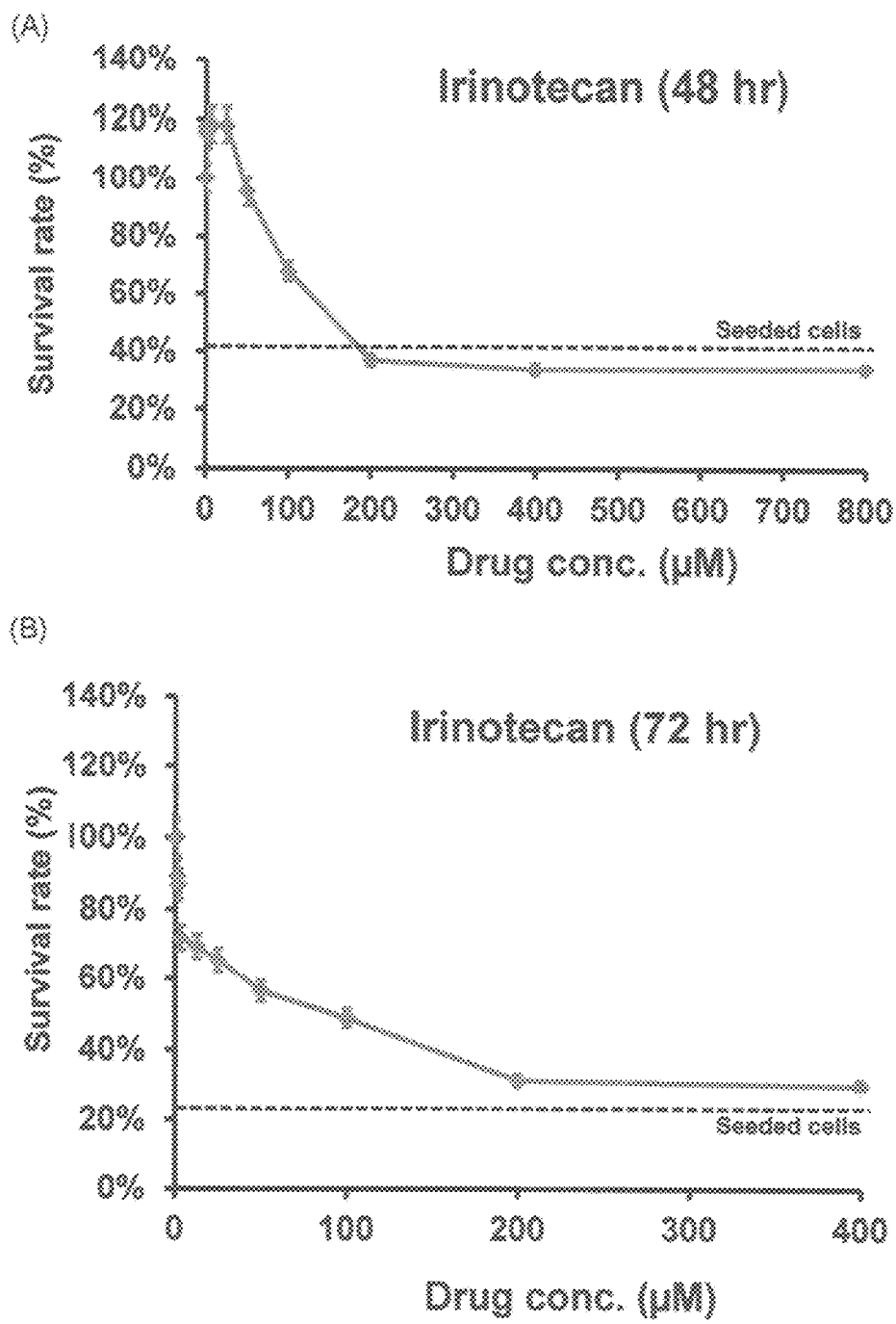
FIG. 5A-B

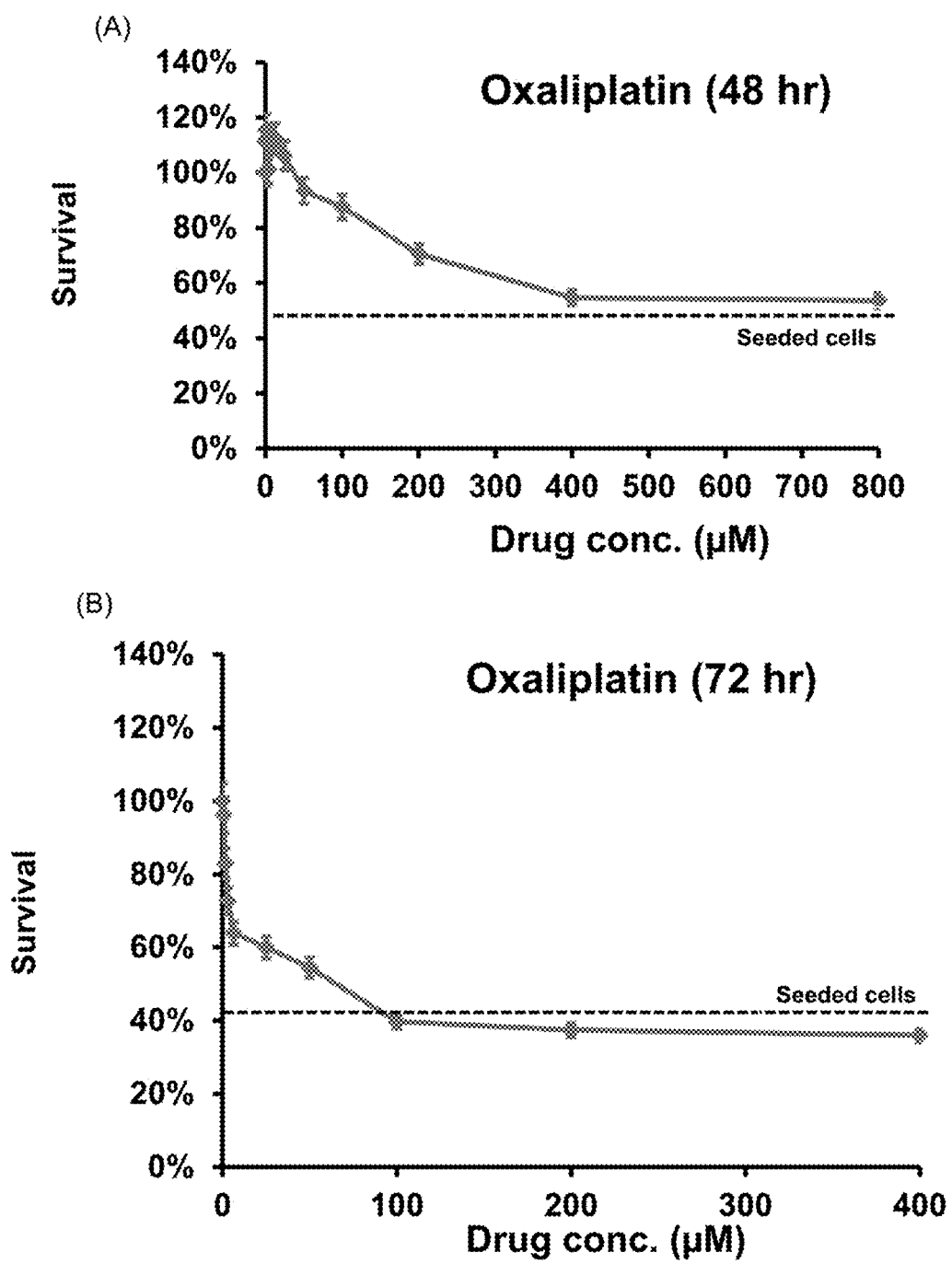
FIG. 6A-B

FIG. 7A-B
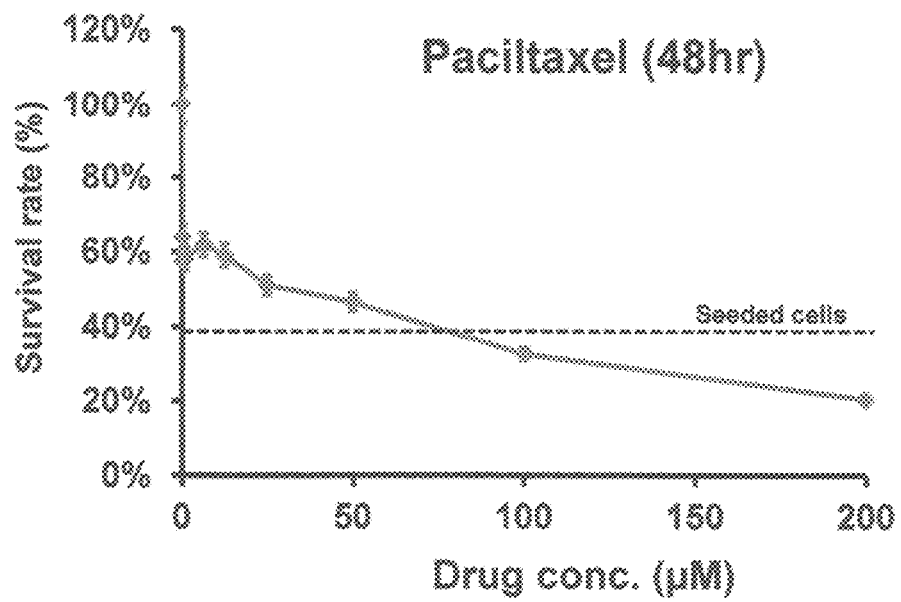
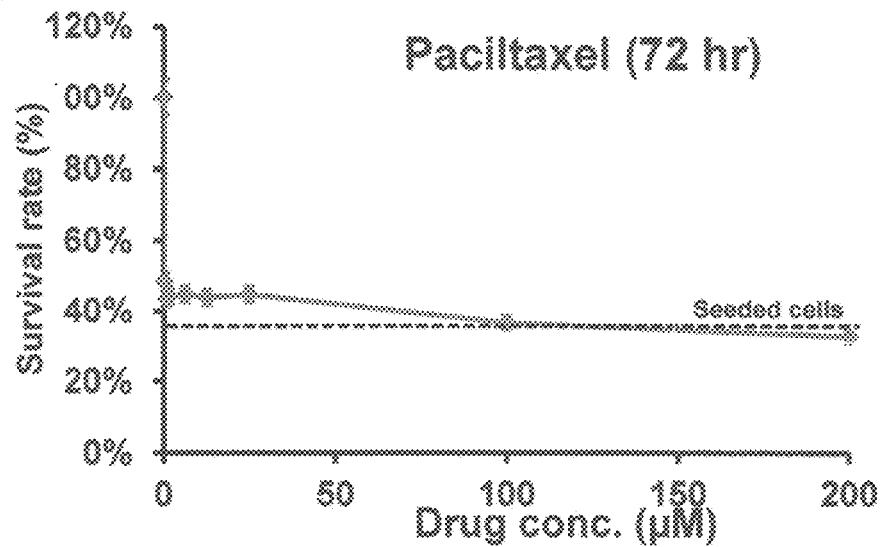

FIG. 10A-C
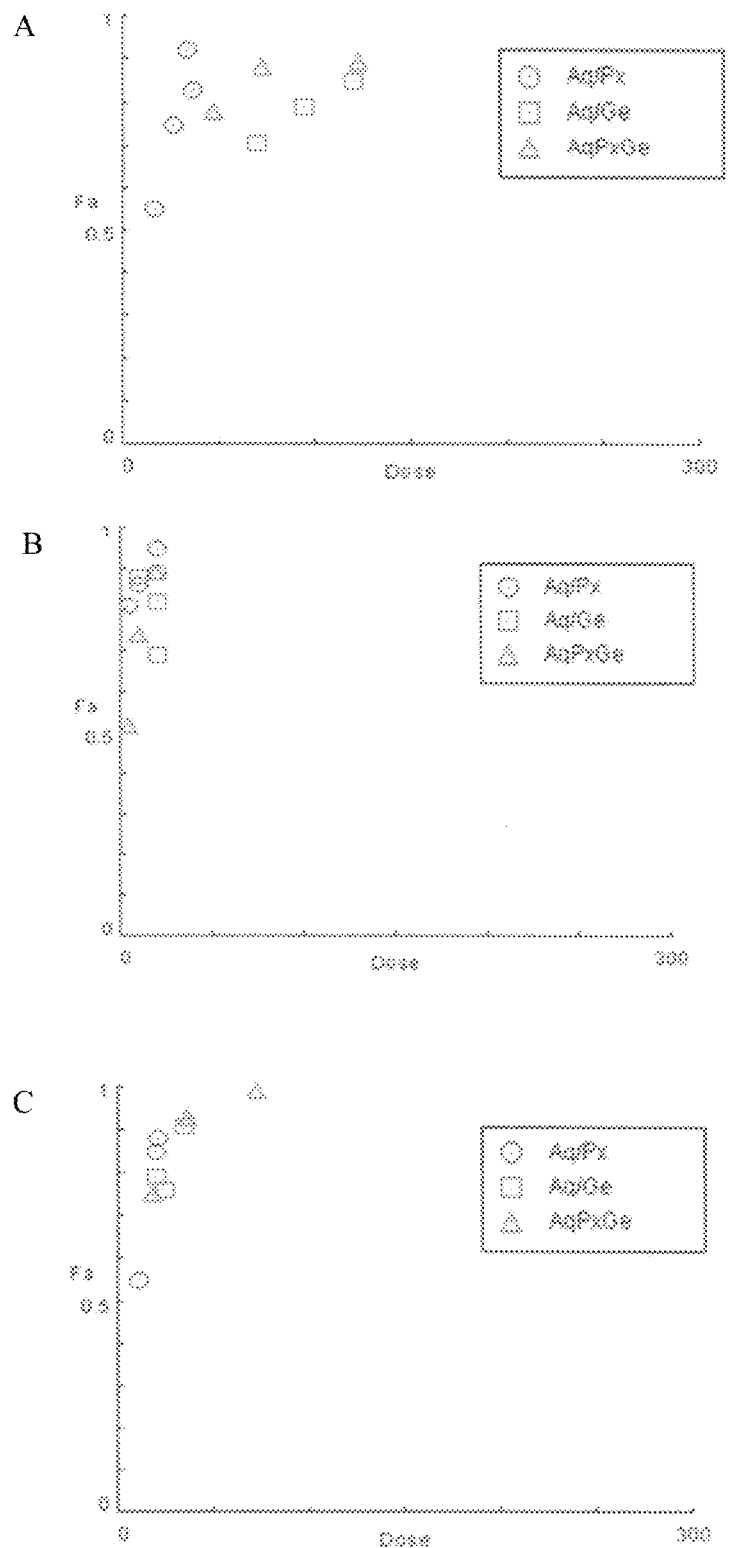

FIG. 11A-C
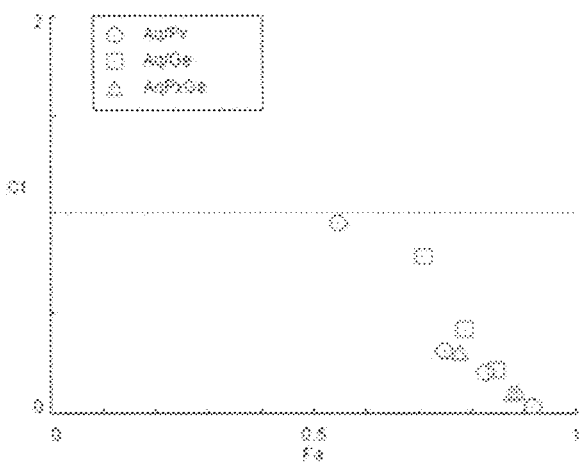
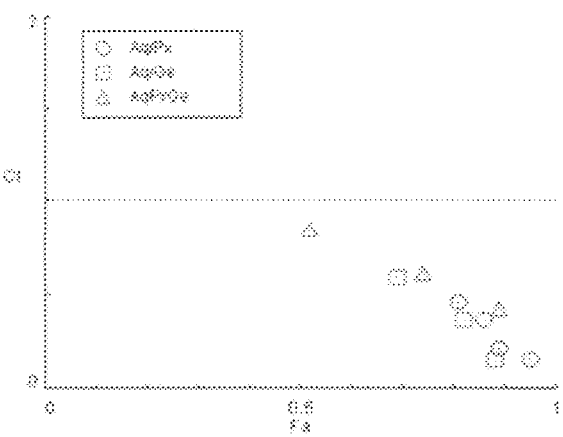
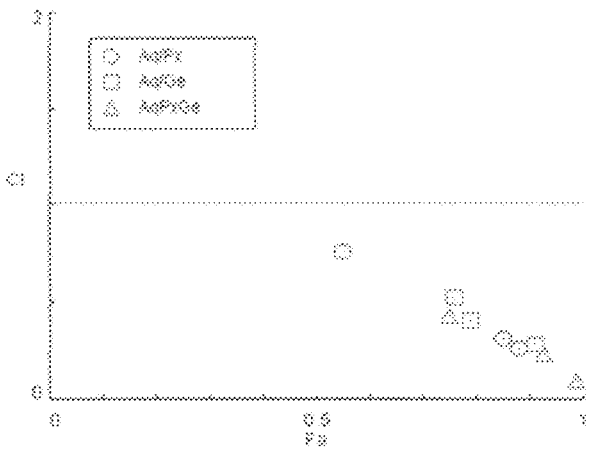

FIG. 18A-B
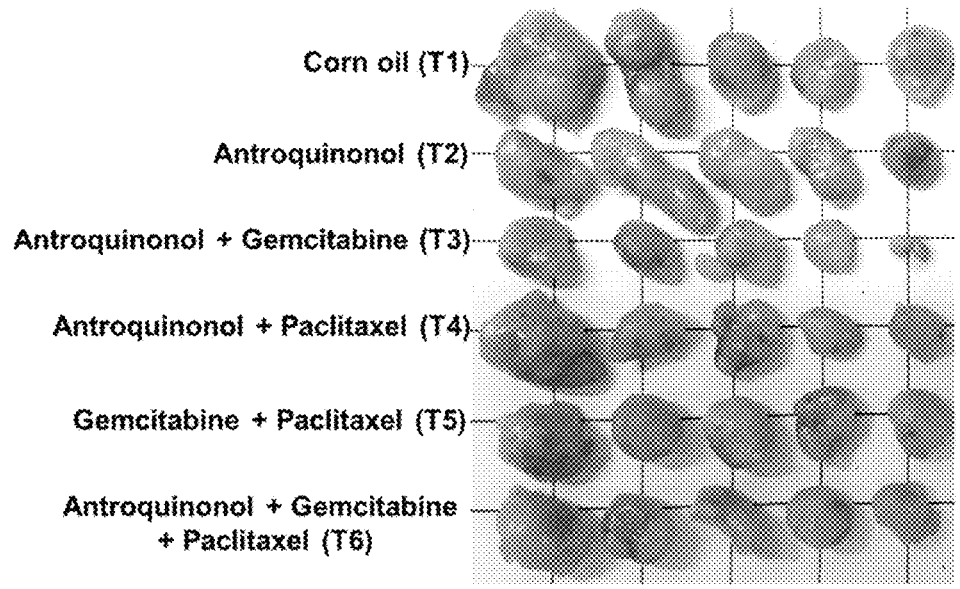
A
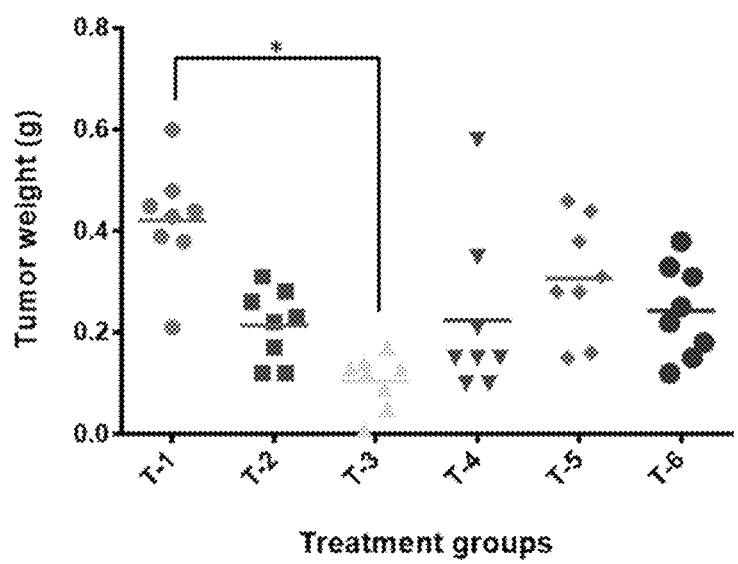
B

THERAPEUTIC COMPOSITIONS FOR TREATING PANCREATIC CANCER

BACKGROUND OF THE INVENTION

Pancreatic cancer arises when cells in the pancreas begin to multiply out of control and form a mass. These cancerous cells have the ability to invade other parts of the body. Pancreatic cancer is the fourth leading cause of cancer death in Western countries and is also the tenth leading cause of cancer death in Taiwan. Approximately 60 percent of pancreatic cancer arises in the head of pancreas, and about 21 percent invades to whole pancreas.

Pancreatic cancer can be divided into two general groups. The vast majority of cases, about 99%, occur in the part of the pancreas which produces digestive enzymes, known as the exocrine component. There are several sub-types of exocrine pancreatic cancers, but their diagnosis and treatment have much in common. These small minority of cancers arise in the hormone-producing (endocrine) tissue of the pancreas.

Surgery with the intention of a cure is only possible in around one-fifth (20%) of new cases. Although CT scans help, in practice, it can be difficult to determine whether the tumor can be fully removed (its "resectability"), and it may only become apparent during surgery that it is not possible to successfully remove the tumor without damaging other vital tissues. Even when the operation appears to have been successful, cancerous cells are often found around the edges ("margins") of the removed tissue. After surgery, adjuvant chemotherapy with gemcitabine or 5-FU can be offered if the person is sufficiently fit, after a recovery period of one to two months. In people not suitable for curative surgery, chemotherapy may be used to extend life or improve its quality of life.

SUMMARY OF THE INVENTION

In one aspect provided herein are composition for treating pancreatic cancer in a subject comprising a compound having the structure:

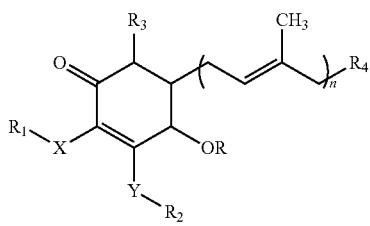

and one or more anti-cancer agents,
wherein each of X and Y independently is oxygen, or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is H, $C_1$-$C_8$alkyl, $C_2$-$C_8$alkenyl, $C_2$-$C_8$alkynyl, or aryl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl; n=1-12; or a pharmaceutically acceptable salt, metabolite, solvate or prodrug thereof.

In another aspect provided herein are methods for treating pancreatic cancer in a subject comprising administering the subject in need thereof of a compound having the structure:

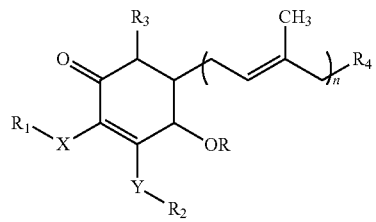

and one or more anti-cancer agents,
wherein each of X and Y independently is oxygen, or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is H, $C_1$-$C_8$alkyl, $C_2$-$C_8$alkenyl, $C_2$-$C_8$alkynyl, or aryl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl; n=1-12; or a pharmaceutically acceptable salt, metabolite, solvate or prodrug thereof.

In another aspect provided herein are methods for the treatment of a patient whose pancreatic cancer is resistant, refractory or non-responsive to gemcitabine, paclitaxel, or a combination thereof, comprising administering to a patient in need thereof a compound having the structure:

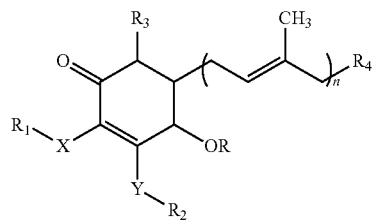

or a pharmaceutically acceptable salt, metabolite, solvate or prodrug thereof,
wherein each of X and Y independently is oxygen, or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is H, $C_1$-$C_8$alkyl, $C_2$-$C_8$alkenyl, $C_2$-$C_8$alkynyl, or aryl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A/B provide the results of cytotoxic activity in AsPC-1 pancreatic cancer cells treated with exemplary compound 1 for (1A) 48 hours and (1B) 72 hours. MTT assay was used to measure cytotoxic activity.

FIG. 2A/B provide the results of cytotoxic activity in AsPC-1 pancreatic cancer cells treated with Erlotinib for (2A) 48 hours and (2B) 72 hours. MTT assay was used to measure cytotoxic activity.

FIG. 3A/B provide the results of cytotoxic activity in AsPC-1 pancreatic cancer cells treated with 5-FU for (3A) 48 hours and (3B) 72 hours. MTT assay was used to measure cytotoxic activity.

FIG. 4A/B provide the results of cytotoxic activity in AsPC-1 pancreatic cancer cells treated with Gemcitabine for (4A) 48 hours and (4B) 72 hours. MTT assay was used to measure cytotoxic activity.

FIG. 5A/B provide the results of cytotoxic activity in AsPC-1 pancreatic cancer cells treated with Irinotecan for (5A) 48 hours and (5B) 72 hours. MTT assay was used to measure cytotoxic activity.

FIG. 6A/B provide the results of cytotoxic activity in AsPC-1 pancreatic cancer cells treated with Oxaliplatin for (6A) 48 hours and (6B) 72 hours. MTT assay was used to measure cytotoxic activity.

FIG. 7A/B provide the results of cytotoxic activity in AsPC-1 pancreatic cancer cells treated with Paclitaxel for (7A) 48 hours and (7B) 72 hours. MTT assay was used to measure cytotoxic activity.

FIG. 10A-C show the dose-effect for combination of Compound 1 (also known as antroquinonol, Aq) with paclitaxel (Px), gemcitabine (Ge) in pancreatic cancer cell lines. Plots indicated the Fa values of the treated of combination of antroquinonol with paclitaxel, antroquinonol with gemcitabine, antroquinonol plus paclitaxel and gemcitabine in AsPC-1 (10A), CaPan-2 (10B) and Panc-1 (10C) pancreatic cancer cell lines. The x-axis represents the dose of drugs in μmol/L and the y-axis represents Fa, the fraction of cell affected (growth inhibition).

FIG. 11A-C show the analysis results of the combinations by Compound 1 with paclitaxel, gemcitabine in pancreatic cancer cell lines for 72 hours. CI plots for the combination of antroquinonol (Aq) with paclitaxel (Px), antroquinonol with gemcitabine (Ge), antroquinonol plus paclitaxel and gemcitabine in AsPC-1 (11A), CaPan-2 (11B) and Panc-1 (11C) pancreatic cancer cell lines. The x-axis represents Fa (fraction of cell affected) and the y-axis represents CI (combination index). CI=1, <1 and >1 indicates additive effect, synergism and antagonism, respectively.

FIG. 18A/B show the result s of the images (18A) and FIG. 18B) of excised tumors at the time of sacrifice from the subcutaneous AsPC-1 pancreatic tumor xenograft-bearing male nude mice after 28 days of treatments. ANOVA was used to analyze the statistical significance. * $P<0.05$ is considered to be statistically significant when compared with control group (T1, corn oil group).

DETAILED DESCRIPTION OF THE INVENTION

Figure 8:
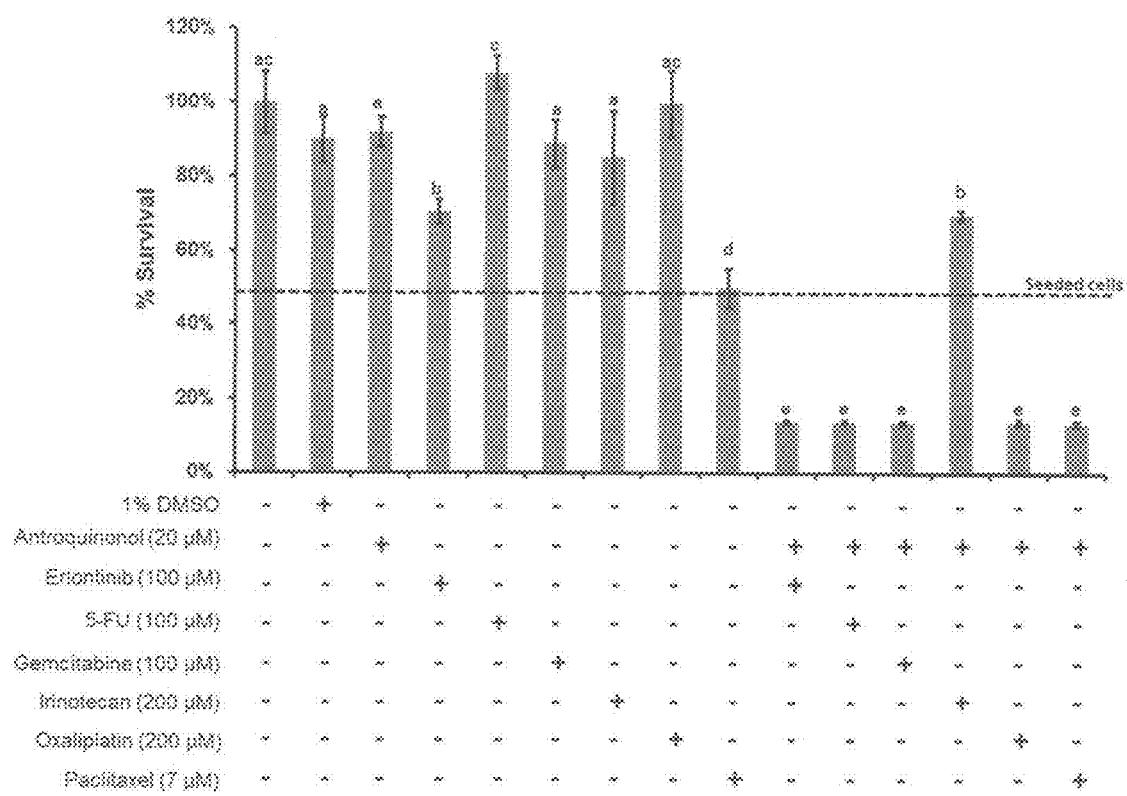
FIG. 8 shows the effect of Compound 1 with chemotherapy drugs, paclitaxel, gemcitabine, 5-FU, oxaliplatin, erlotinib or irinotecan on the cytotoxicity of AsPC-1 pancreatic cancer cell line for 48 hours. MTT assay was used to measure cytotoxic activity. Values are means of survival rate±SEM. Different letters (a-e) denote significant difference ($P<0.05$) for various treatments.

Surgery with the intention of a cure is only possible in around one-fifth (20%) of new cases. Although curative surgery no longer entails the very high death rates that occurred until the 1980s, a high proportion of people (about 30-45%) still have to be treated for a post-operative sickness that is not caused by the cancer itself. The most common complication of surgery is difficulty in emptying the stomach. After surgery, adjuvant chemotherapy with gemcitabine or 5-FU can be offered if the person is sufficiently fit, after a recovery period of one to two months. Gemcitabine was approved by the United States Food and Drug Administration (FDA) in 1997, after a clinical trial reported improvements in quality of life and a 5-week improvement in median survival duration in people with advanced pancreatic cancer. Chemotherapy using gemcitabine alone was the standard for about a decade, as a number of trials testing it in combination with other drugs failed to demonstrate significantly better outcomes.

The FOLFIRINOX chemotherapy regimen using four drugs was found more effective than gemcitabine, but with substantial side effects, and is thus only suitable for people with good performance status. This is also true of protein-bound paclitaxel (nab-paclitaxel), which was licensed by the FDA in 2013 for use with gemcitabine in pancreas cancer. However, the changes of the last few years have only increased survival times by a few months.

A method for treating pancreatic cancer in a subject comprising administering the subject in need thereof a cyclohexanone compound was reported in U.S. Pat. No. 8,236,860. An exemplary compound, Antroquinonol was studied for treating pancreatic cancer using the orthotopic PANC-1 human pancreatic cancer xenograft model. Four groups of mice were treated with 30 mg/kg, 60 mg/kg, 90 mg/kg, and vehicle control, respectively. Treatment with antroquinonol at 30, 60, and 90 mg/kg produced an effective anti-tumor activity with statistically significant smaller mean tumor volumes and tumor weights in all three dosage levels compared to vehicle control. Although Antroquinonol was shown to be a good candidate as a drug to treat pancreatic cancer, there was no consideration to use it in any combination therapy.

However, it is found unexpectedly a synergistic effect existed in a combination therapy comprising a compound having the structure:

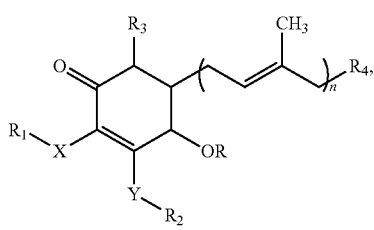

and one or more anti-cancer agents, such as gemcitabine, paclitaxel, or a combination thereof provides synergistic effects compared with the mono therapy; wherein each of X and Y independently is oxygen, or sulfur;

R is a hydrogen or C(=O)$C_1$-$C_8$alkyl;

each of $R_1$, $R_2$ and $R_3$ independently is a hydrogen, methyl or $(CH_2)_m$—$CH_3$;

$R_4$ is H, $C_1$-$C_8$alkyl, $C_2$-$C_8$alkenyl, $C_2$-$C_8$alkynyl, or aryl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

n=1-12; or a pharmaceutically acceptable salt, metabolite, solvate or prodrug thereof. In some embodiments, such combination therapy further comprises administering an immunotherapy agent.

In some embodiments, provided herein are compositions for treating pancreatic cancer in a subject comprising a compound having the structure:

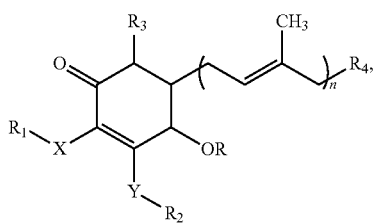

and one or more anti-cancer agents, (see Examples 1-3). The cyclohexenone compounds, in some embodiments, are obtained from extracts of natural products and in some other embodiments, are prepared synthetically. See for example, U.S. Pat. No. 9,365,481.

In some embodiments, the one or more anti-cancer agents comprise gemcitabine, paclitaxel, idarubicin/cytarabine, etopside phosphate, gleevec (imatinib), temozolomide, bortezomib, letrozole, cetuximab, bevacizumab, nab-paclitaxel, docetaxel, erlotinib, pemetrexed, pemetrexed/carboplatin, paxlitaxel/carboplatin, letrozole/cyclophsphamide, temsirolimus, bevacizumab/temsirolimus, 1pilimumab, RAD001, Pazopanib, FOLFIRI, BKM120, GSK1120212, PF-05212384/irinotecan, AZD2171, PF-04691502, cyclophosphamide, cisplatin, cytarabine/daunorubcin, tersirolimus, erlotinib/temsirolimus, capecitabine, tamoxifen, bortezomib, trastuzumab, docetaxel/capecitabine, trastuzumab/tipifarnib, tipifarnib/gemcitabline, tootecan, or combinations thereof. In certain embodiments, the one or more anti-cancer agent is gemcitabine, paclitaxel, or a combination thereof. In certain embodiments, the one or more anti-cancer agent are the combination of gemcitabine and paclitaxel.

For example, paclitaxel is classified as a "plant alkaloid," a "taxane" and an "antimicrotubule agent." It is used to treat a number of types of cancer such as ovarian cancer, breast cancer, lung cancer, Kaposi sarcoma, cervical cancer, and pancreatic cancer. Albumin-bound paclitaxel (trade name Abraxane, also called nab-paclitaxel) is an alternative formulation where paclitaxel is bound to albumin nano-particles. Paclitaxel is known to have some common side effects including nausea and vomiting, loss of appetite, change in taste, thinned or brittle hair, pain in the joints of the arms or legs lasting two to three days, changes in the color of the nails, and tingling in the hands or toes. Paclitaxel is one of several cytoskeletal drugs that target tubulin. Paclitaxel-treated cells have defects in mitotic spindle assembly, chromosome segregation, and cell division. Unlike other tubulin-targeting drugs such as colchicine that inhibit microtubule assembly, paclitaxel stabilizes the microtubule polymer and protects it from disassembly.

Another exemplary anticancer drug, gemcitabine is a nucleoside analog used as chemotherapy to treat a number of types of cancer including breast cancer, ovarian cancer, non-small cell lung cancer, pancreatic cancer, and bladder cancer. Common side effects include bone marrow suppression, liver and kidney problems, nausea, fever, rash, shortness of breath, and hair loss. Use during pregnancy will likely result in harm to the baby. Gemcitabine is in the nucleoside analog family of medication. It works by blocking the creation of new DNA, which results in cell death.

In some embodiments, there are provided methods for treating pancreatic cancer in a subject comprising administering the subject in need thereof the combination therapy compositions described herein.

In some embodiments, there are provided methods for the treatment of a patient whose pancreatic cancer is resistant, refractory or non-responsive to gemcitabine, paclitaxel, or a combination thereof, comprising administering the patient in need thereof a compound having the structure:

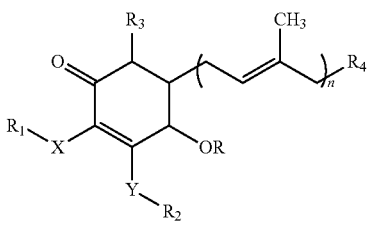

or a pharmaceutically acceptable salt, metabolite, solvate or prodrug thereof. In some embodiments, the methods further comprise administering an immunotherapy agent.

In certain embodiments, the cancer is resistant, refractory or non-responsive to a drug selected from gemcitabine, paclitaxel, idarubicin/cytarabine, etopside phosphate, gleevec, temozolomide, bortezomib, letrozole, cetuximab, bevacizumab, nab-paclitaxel, docetaxel, erlotinib, pemetrexed, pemetrexed/carboplatin, paxlitaxel/carboplatin, letrozole/cyclophsphamide, temsirolimus, bevacizumab/temsirolimus, 1pilimumab, RAD001, Pazopanib, FOLFIRI, BKM120, GSK1120212, PF-05212384/irinotecan, AZD2171, PF-04691502, cyclophosphamide, cisplatin, cytarabine/daunorubcin, tersirolimus, erlotinib/temsirolimus, capecitabine, tamoxifen, bortezomib, trastuzumab, docetaxel/capecitabine, trastuzumab/tipifarnib, tipifarnib/gemcitabline, tootecan, or combinations thereof. In certain embodiments, the cancer is resistant, refractory or non-responsive to gemcitabine or paclitaxel. In certain embodiments, the cancer is resistant, refractory or non-responsive to a combination of gemcitabine and paclitaxel.

In some embodiments, the cyclohexenone compound having the structure

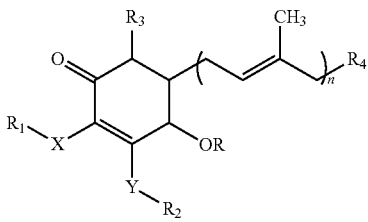

is prepared synthetically or semi-synthetically from any suitable starting material. In other embodiments, the cyclohexenone compound is prepared by fermentation, or the like. For example, Compounds 1, 3 and 4 are isolated from organic solvent extracts or prepared synthetically or semi-synthetically. The non-limited exemplary compounds are illustrated below.

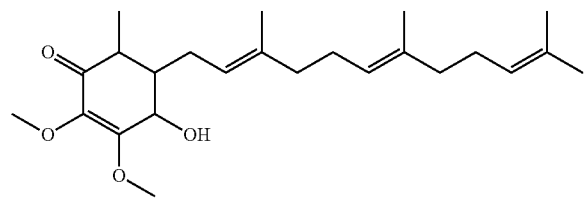

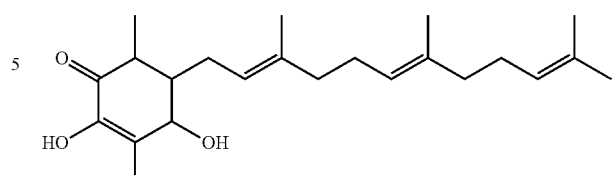

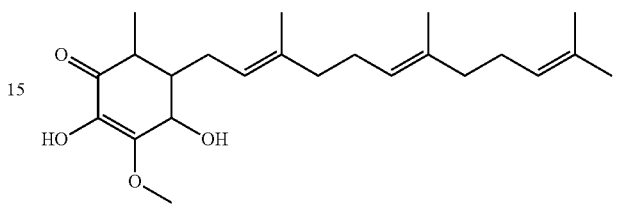

In some embodiments, R is a hydrogen, $C(=O)C_3H_7$, $C(=O)C_2H_5$, or $C(=O)CH_3$. In some embodiments, $R_1$ is a hydrogen or methyl. In certain embodiments, $R_2$ is a hydrogen, methyl, ethyl, propyl, butyl, pentyl or hexyl. In some embodiments, $R_3$ is a hydrogen, methyl, ethyl, propyl, butyl, pentyl or hexyl. In some embodiments, $R_4$ is hydrogen. In some embodiments, $R_4$ is $C_1$-$C_8$alkyl, $C_2$-$C_8$alkenyl, $C_2$-$C_8$alkynyl, or aryl, optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2CH=C(CH_3)_2$. In certain embodiments, the compound is

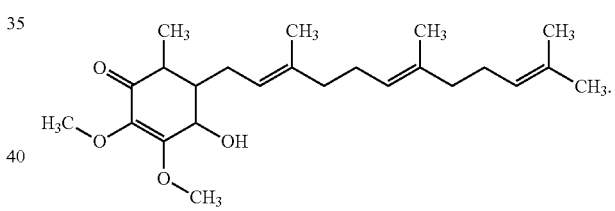

In some embodiments, the methods to treat pancreatic cancer described herein comprise administering an immunotherapy agent. The immunotherapy agent includes, without limitation, any living immune cell that can be administered to a patient, and/or antibodies specific for a target cell (e.g., a tumor cell such as pancreatic cancer cell). Preferably, the immunotherapy agent is an NK cell or a T cell, or a modification or derivative thereof.

Immunotherapy

Immunotherapy is the "treatment of disease by inducing, enhancing, or suppressing an immune response". Immunotherapies designed to elicit or amplify an immune response are classified as activation immunotherapies, while immunotherapies that reduce or suppress are classified as suppression immunotherapies.

In some embodiments, the immunotherapy agent is an anti-cancer antibody. Non-limiting examples include trastuzumab (Herceptin®), bevacizumab (Avastin®), cetuximab (Erbitux®), panitumumab (Vectibix®), ipilimumab (Yervoy®), rituximab (Rituxan®), alemtuzumab (Campath®), ofatumumab (Arzerra®), gemtuzumab ozogamicin (Mylotarg®), brentuximab vedotin (Adcetris®), $^{90}$Y-ibritumomab tiuxetan (Zevalin®), $^{131}$I-tositumomab (Bexxar®), anti-programmed-death 1 (anti-PD-1) antibody such as Nivolumab, Pembrolizumab, and the like.

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as, "$C_1$-$C_{12}$ alkyl", "$C_1$-$C_8$ alkyl" or similar designations. By way of example only, "$C_1$-$C_8$ alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{12}$ alkylene. In another aspect, an alkylene is a $C_1$-$C_8$ alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$ aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. The alkenyl group of the compounds described herein may be designated as, "$C_2$-$C_{10}$ alkenyl", "$C_2$-$C_8$ alkenyl" or similar designations. By way of example only, "$C_2$-$C_8$ alkenyl" indicates that there are two, three, four, five, six, seven or eight carbon atoms in the alkenyl chain. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkynyl" as used herein, means a straight, branched chain, or cyclic (in which case, it would also be known as a "cycloalkynyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). The alkynyl group of the compounds described herein may be designated as, "$C_2$-$C_{10}$ alkynyl", "$C_2$-$C_8$ alkynyl" or similar designations. By way of example only, "$C_2$-$C_8$ alkynyl" indicates that there are two, three, four, five, six, seven or eight carbon atoms in the alkynyl chain. In some embodiments, alkynyl groups are optionally substituted. Illustrative examples of alkynyl include, but are not limited to, ethynyl, propynyl, butynyl, pentynyl, hexynyl, heptynyl, and the like.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

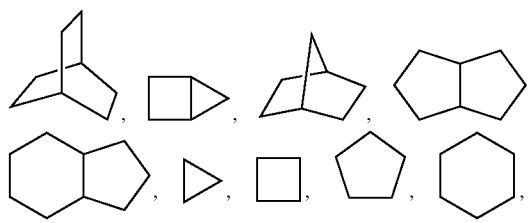

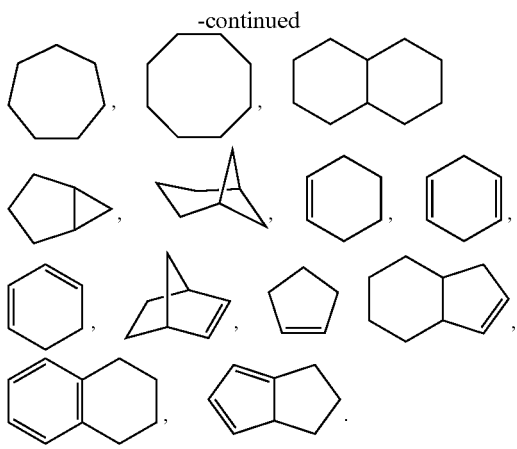

In some embodiments, depending on the structure, a cycloalkyl group is a monoradical or a diradical (e.g., a cycloalkylene group).

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration and Dosage

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized. In certain embodiments, the cyclohexenone compound is

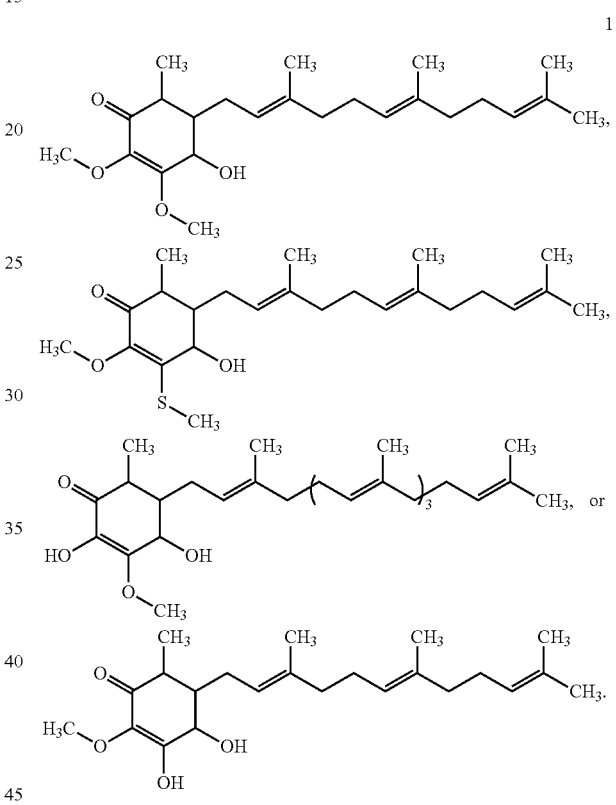

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

General Consideration for Combination Treatments

In general, the compositions described herein and, in embodiments where combinational therapy is employed and described herein, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

EXAMPLES

Example 1. Preparation of the Exemplary Cyclohexenone Compounds

Via a particular herbal purification procedure: the following procedure is for illustration purposed only. The other purification methods may be used as well.

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of $C_{24}H_{38}O_4$, molecular weight of 390 with melting point of 48 to 52° C. NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)=12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

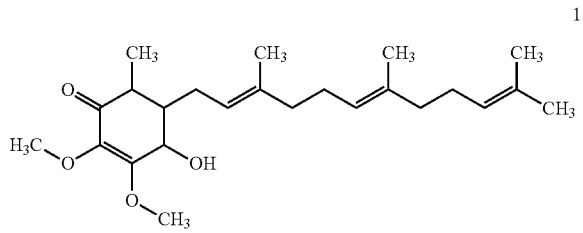 [SMILES: COC1=C(OC)C(O)C(C/C=C(\C)CC/C=C(\C)CCC=C(C)C)C(C)C1=O]

Compound 1: 4-hydroxy-2,3-dimethoxy-6-methyl-5-(3,7,11-trimethyldodeca-2,6,10-trienyl)cyclohex-2-enone Other compounds where $R_4$ is H, $C_1$-$C_8$alkyl, $C_2$-$C_8$alkenyl, $C_2$-$C_8$alkynyl, or aryl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl were obtained as well.

Alternatively, the exemplary compounds may be prepared synthetically. See for example, U.S. Pat. No. 9,365,481. Similarly, other cyclohexenone compounds having the structure

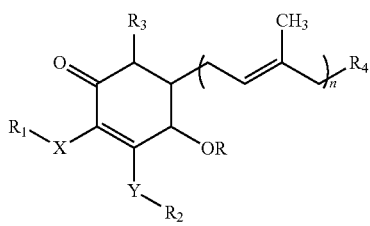

are isolated from *Antrodia camphorata* or prepared synthetically or semi-synthetically from the suitable starting materials. An ordinary skilled in the art would readily utilize appropriate conditions for such synthesis.

Example 2. Study of Compound 1 with Clinical Chemotherapy Drugs on Human Pancreatic Carcinoma in AsPC-1 Cell Culture System and in a Severe Combined Immunodeficient Mouse Xenograft Tumor Model In order to evaluate the efficacy of a combination therapy comprising the exemplary compound 1 with an anticancer agent (e.g., any clinically used drugs) for the treatment of pancreatic carcinoma development, an in vitro study and an in vivo xenografts study by an exemplary Compound 1 with selected current clinical chemotherapy drugs were conducted.

For in vitro study, Compound 1 and each of the selected six (6) clinical chemotherapy drugs were used on human pancreatic carcinoma AsPC-1 and/or CaPan-2, PANC-1 in cell culture system.

In in vivo xenograft mouse model, gemcitabine and/or paclitaxel were selected to be administered via tail vein twice a week with an oral administration of Compound 1 once a day for a total of 28 doses on human pancreatic carcinoma AsPC-1 xenograft model.

In Vitro Test:

The human pancreatic carcinoma cell lines, AsPC-1, PANC-1 and CaPan-2 were seeded $3\times10^4$ cells per well and cultured in a forty-eight (48) well cell culture dish (growth area 0.95 cm$^2$ per well). Sixteen (16) hours later, cells were treated Compound 1 alone or Compound 1 with a clinical chemotherapy drug, respectively. After 48 or 72 hours of the treatment, methylthiazoletetrazolium (MTT) assay (supplemental protocol-1) was performed to measure the effect of treatment on the viability of cells during proliferation.

In Vivo Test:

The human pancreatic carcinoma cell line, AsPC-1, was cultured and the cells were injected subcutaneously in a flank of 60 mice. Three days later, the tumors could be felt in the mice. When tumors reached approximately 100-200 mg (mm$^3$), total of fifty one (51) tumor-bearing mice were randomly selected and sorted into one of six (6) groups. Vehicle (corn oil) treated mice were used as negative controls. Compound 1 combined with gemcitabine or paclitaxel were administered orally once a day and/or I.V. twice a week for four (4) weeks. Tumor measurements were recorded once a week using hand-held calipers and Visualsonic Vevo 2100 image system. Individual mouse weights were taken once a week during dosing. Mice were monitored daily for signs of toxicity and morbidity; any abnormal findings were recorded. The study was terminated four (4) weeks after initiation of drug administration.

Mice were euthanized when an individual mouse has a tumor that is 2,000 mg (cm$^3$) over one (1) measurement. A mouse was moribund when a tumor impedes the mouse's ability to feed, drink or ambulate, or if a mouse loses >20% of its original body weight. An individual group was euthanized when tumors reached a mean target size of 1,500 mg per group over two (2) consecutive measurements. The study coordinators should be notified of any unscheduled euthanasia. The study was terminate four (4) weeks after the initiation of drugs administration.

Test System

A. Cell Lines:
Human pancreatic carcinoma AsPC-1 (ATCC Catalog No. CRL-1682).
Human pancreatic carcinoma PANC-1 (ATCC Catalog No. CRL-1469).
Human pancreatic carcinoma CaPan-2 (ATCC Catalog No. HTB-80).

B. Cell Preparation
1. Remove and discard culture medium.
2. Briefly rinse the cell layer with 5 mL HBSS. Gently shake and remove the HBSS.
3. Add 5 mL trypsin-EDTA to 15 cm$^2$ polystyrene dishes. Incubate 5 mins at 37° C. in a humidified incubator with 95% air/5% CO$_2$ atmosphere.
4. Add 5 mL of complete growth medium (DMEM medium containing 10% FBS) and aspirate cells by gently pipetting.
5. Count live cells using the trypan blue exclusion assay (supplemental protocol-2) with a hemocytometer.
6. For in vitro study, cells will be seeded $3\times10^4$ cells per well and cultured in a forty-eight (48) wells cell culture dish for sixteen (16) hours until treatment.
7. Incubate cultures at 37° C.

C. Animal Species/Strain:
a. Nude mice, BALB/cAnN.Cg-Foxnl$^{nu}$/CrlNarl
b. Female, athymic nude mice (nu/nu) 4-6 wk of age.
c. Body weight: between 15 and 20 g on the day of inoculation of tumor cells.

D. Human Pancreatic Carcinoma Xenograft Models:
1. To create the subcutaneous xenograft model, athymic female nude mice (4-6 weeks old) were subcutaneously inoculated with $1\times10^7$ AsPC-1 cells in 0.1 mL of serum-free DMEM medium containing 20% Matrigel (BD Biosciences, Bedford Mass.).

2. Tumor-bearing animals were divided into the following 6 groups as table 1.

3. The mice were monitored for activity and physical condition every day, and the determination of body weight and measurement tumor mass should be done once a week. Tumor image will be photed by digital camera and Visualsonic Vevo 2100 image system. Tumor mass is determined by caliper measurement in two perpendicular diameters of the implant and calculate using the formula $(4/3) \times (\pi \times a \times b^2)$, where "a" stands for the long diameter and "b" is the short diameter.

E. Test Articles:

The clinical chemotherapy drugs were purchased from Sigma-Aldrich Co. LLC, and prepared in the following manner:

Erlotinib (Stock conc. 100 mM in DMSO, Sigma Cat. #E4997).

5-Fluorouracil (Stock conc. 100 mM, Sigma Cat. #F6627).

Gemcitabine (Stock conc. 100 mM in DMSO, Sigma Cat. #G6423).

Irinotecan (Stock conc. 100 mM in DMSO, Sigma Cat. #I1406).

Oxaliplatin (Stock conc. 50 mM in DMSO, Sigma Cat. #O9512).

Paclitaxel (Stock conc. 10 mM in DMSO, Sigma Cat. #T7402).

For in vivo test, gemcitabine (G) was purchased from Eli Lilly (Indianapolis, Ind., USA), and paclitaxel (P) was purchased from Sigma-Aldrich.

F. In Vitro Experiment Design:

a. Cytotoxicity of test articles ($TC_{50}$): AsPC-1 was seeded $3 \times 10^4$ cells (counted by Cell counter, LUNA™ Automated Cell Counter or hemocytometer) per well and cultured in a 48 wells cell culture dish. Cells were treated with single article from 400 or 800 μM with serial dilution to 0 μM. After 48 or 72 hours of treated, MTT assay was performed to measure the effect of treatment on the viability of AsPC-1 cells during proliferation. The absorbance at 595 nm was measured using a microplate reader (BioTEK, Synergy™ H1). Article sensitivity curves and $TC_{50}$ values were calculated using GraphPad Prism 4.0 software.

b. Combination therapy of Compound 1 and chemotherapy drugs: This study also contains the cytotoxicity of Compound 1 plus a chemotherapy drug of selections to investigate the efficacy of such combination. Compound 1 combined each of paclitaxel, gemcitabine, 5-FU, oxaliplatin, erlotinib, and irinotecan, respectively. After treated 72 hours, MTT assay was performed to measure the effect of treatment on the viability of AsPC-1 cells during proliferation. The absorbance at 595 nm was measured using a microplate reader.

c. Evaluation of drug interactions: MTT assay was also performed to test the effect of drug combinations on the viability of AsPC-1, PANC-1 and CaPan-2 cell lines. The combination index (CI) isobologram method of Chou and Talalay (Chou and Talalay, 1984; Chang and Chou, 2000) which is based on the median-effect principle, was used to calculate synergism or antagonism for the combined drug effects. Dose-effect curves for each drug, separately and in combination, in serially diluted concentrations were plotted using the median-effect equation and plot (Chou, 1991) and the CI equation and plot (Chou et al., 1994). CI values at different effect and dose levels and isobolograms were generated automatically using the computer software CompuSyn (Chou and Martin, 2005). With this method, additive, synergistic, or antagonistic effects are indicated by CI values of 1, <1, and >1, respectively.

G. In Vivo Experiment Design:

a. Cell Injections: Mice were injected subcutaneously into the right lateral thorax with $1 \times 10^7$ viable human pancreatic carcinoma AsPC-1 Cells. A total of 60 mice were injected, with approximately 36 tumor-bearing mice were used on this study.

b. Selections of animals and group Assignment: This study contained six (6) groups and each group included eight (8) or nine (9) mice respectively. When tumors reached a target window size of approximately 100-200 mg ($mm^3$), 54 tumor-bearing mice were randomly selected and sorted into one of 6 groups. Groups 1 is a solvent treated negative control and contained mice receiving treatment-1. Group 2, 3, 4, 5 and 6 contained mice that received treatment-2, treatment-3, treatment-4, treatment-5 and treatment-6, respectively. Table 1 lists test articles concentrations, solvent articles and dosing schedule.

c. Dose Preparation:

c-1: Compound 1 (A)

i. Weighed an appropriate amount of Compound 1 and added into a 50 mL tube.

ii. Added an appropriated amount of corn oil (Sigma-Aldrich) into the 50 mL tube. Mixed the formulation with vortex until homogenized completely. Pulled the formulation up into a disposable syringe and transferred to 4 mL brown tubes, 3.2 mL/tube.

iii. Stored the suspension at frozen conditions (−20° C.) until used.

iv. Completely thawed the formulation in a 37° C. water bath on day of intended use.

c-2: Gemcitabine (G)

i. Stock of gemcitabine was stored as a 50 mg/mL solution in sterile PBS at −20° C. (Ito et al., 2006; Awasthi et al., 2013).

ii. Before animal studies, weighed an appropriate amount of gemcitabine into a 4 mL tube.

iii. Added an appropriate volume of vehicle-I (50% Ethanol & 50% Tween-80 (v/w)) into the 4 mL tube and shook until the material dissolved completely.

iv. Added an appropriate volume of physiological saline into the 4 mL tube and moved the tube side-by-side to completely homogenize the solution.

c-3: Paclitaxel (P)

i. Stock of paclitaxel was dissolved in 100% ethanol to final concentration 10 mg/mL (Shi et al., 2000; Chang et al., 2006; Awasthi et al., 2013).

ii. Before animal studies, weighed an appropriate amount of paclitaxel into a 4 mL tube.

iii. Added an appropriate volume of vehicle-$I^b$ into the 4 mL tube and shook until the material dissolved completely.

iv. Added an appropriate volume of physiological saline into the 4 mL tube and moved the tube side-by-side to completely homogenize the solution.

TABLE 1

Treatment groups of AsPC-1 xenograft:

| Group Number | Treatment label | Dose/mouse/ day or time | Dosing Route | Dose volume/ mouse | Frequency |
|---|---|---|---|---|---|
| 1 | Treatment -1 | Solvent (corn oil) | oral | 100 μL for oral, | Orally once a |

TABLE 1-continued

Treatment groups of AsPC-1 xenograft:

| Group Number | Treatment label | Dose/mouse/ day or time | Dosing Route | Dose volume/ mouse | Frequency |
|---|---|---|---|---|---|
| 2 | Treatment -2 | A (120 mg/kg) | oral (A) | 20-30 uL for I.V. | day, I.V. twice weekly for 4 weeks. |
| 3 | Treatment -3 | A (120 mg/kg) G (100 mg/kg) | oral (A)/ IV (G) | | |
| 4 | Treatment -4 | A (120 mg/kg) P (5 mg/kg) | oral (A)/ IV (P) | | |
| 5 | Treatment -5 | G (100 mg/kg) P(5 mg/kg) | IV (G & P) | | |
| 6 | Treatment -6 | G (10 mg/kg) P (30 mg) A(120 mg/kg) | oral (A) IV (G & P) | | |

Observations and Examinations of In Vivo System

A. Clinical Observations: Clinical observations of each study animal were performed and at least once daily (including weekends and holidays) for signs of morbidity, mortality and Test Article toxicity. Morbidity includes signs of illness such as, but not limited to, emaciation, dehydration, lethargy, hunched posture, unkempt appearance, dyspnea and urine or fecal staining. All abnormal findings will be recorded.

B. Animal Weights: Individual animal weights were taken one (1) time per week after/before dosing. Weights were recorded first prior to cell injections and continued for the duration of the study.

C. Tumor Measurements: The injection site of each animal was monitored one (1) time per week for signs of tumor growth. Throughout the study, the length (a) and width (b) of any tumors developed were measured in millimeters (mm) using vernier calipers, where a is the longer of the two (2) dimensions. The applicable tumor size in millimeter (mm) or centimeter (cm) was calculated by using the formula associated with a prolate ellipsoid: $M=(4/3)\times(\pi\times a\times b^2)$; and these data was recorded.

D. Evaluation of drug synergistic effect by tumor growth inhibition (TGI) and tumor inhibitory ratio (TIR): Volume of tumor growth inhibition (TGI) for each group was calculated according to the following formula:

Tumor growth inhibition (%)=$(1-[T-T_0]/[C-C_0])\times 100$

T and $T_0$ are the mean tumor volumes on the end day and day 1 of treatment, respectively, for the experimental groups. For the control groups, C and $C_0$ are the mean tumor volumes on a end day and the start of the study, respectively.

For TIR, at the 4th week after treatment, the mice were sacrificed, and tumors were ablated carefully and weighed after any remaining blood was washed off with PBS. The tumor inhibitory ratio was calculated by the formula:

Tumor inhibitory ratio (%)=$[(W_{Control}-W_{Treated})/W_{Control}]\times 100\%$ $W_{Treated}$ and $W_{Control}$ are the average tumor weights of the treated and control mice, respectively.

D. Hematological parameters: Cardiac blood was collected in EDTA for analyzing hematological parameters such as white blood cell count (WBC), red blood cell count (RBC), hemoglobin concentration (HB), hematocrit, mean corpuscular hemoglobin and concentration, platelet distribution width, platelet count, neutrophils, lymphocytes, monocytes, eosinophils. This was determined using hematology counter (Abbott Cell-Dyn 3700, IL).

Statistical analysis: All data are presented as mean±standard error of the mean (SEM). One-way analysis of variance (ANOVA) was used to determine significance between groups. For multiple comparisons of more than two groups, the ANOVA analysis was used and followed by post-hoc tests with the Bonferroni correction. A value of $P<0.05$ was considered to be significant.

Illustration of Daily Schedule of Xenograft Study
  AsPC-1 implanted 8 days; AsPC-1 human pancreatic carcinoma cells implanted day—day 1
  Treatment plan: every day oral and every 4 day injection
  Every week do Tumor measurement and Body weight
  End study at day 28
  Treatment frequency: Orally once a day, I.V. twice weekly for 4 weeks
  Administered study groups with treatments orally every day for 28 days with treatment-1 treatment-2, treatment-3, treatment-4, treatment-5, and treatment-6
  Treatment-4, treatment-5 and treatment-6 include injection (IV) at day 1, 5, 9, 12, 16, 20, 23, and 27
  Tumor measurement and body weight at day 1, 8, 15

Results

Figure 9:
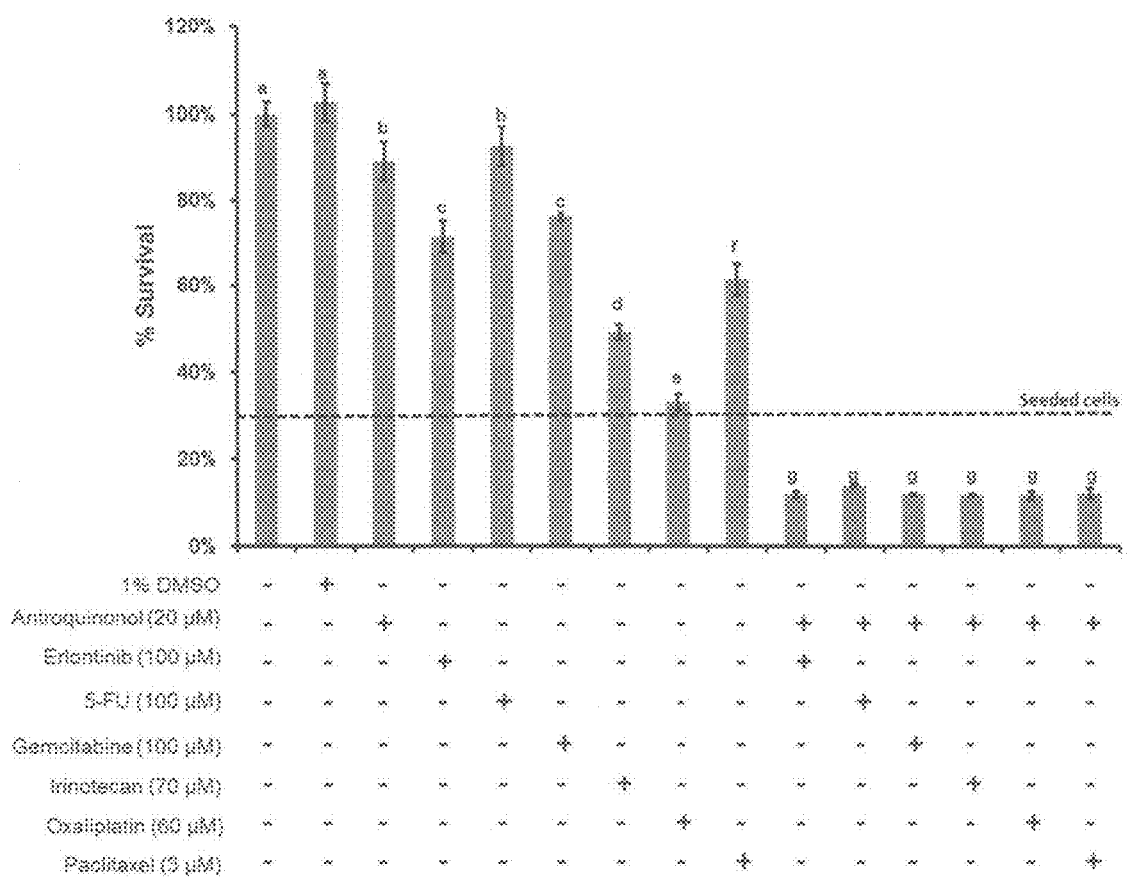
FIG. 9 shows the cytotoxic activity of Compound 1 with chemotherapy drugs, paclitaxel, gemcitabine, 5-FU, oxaliplatin, erlotinib and irinotecan, respectively. AsPC-1 pancreatic cancer cells were treated antroquinonol or combination formula for or 72 hours. MTT assay was used to measure cytotoxic activity. Values are means of survival rate±SEM. Different letters (a-g) denote significant difference ($P<0.05$) for various treatments.

In vitro cytotoxicity: To evaluate the combinatorial therapeutic efficiency of the exemplary compound 1, the viability of treated AsCp-1 cell lines using 3-(4,5-dimethylthiazol-2-yl)-2,5-diphenyltetrazolium bromide (MTT) assay was measured. The toxic concentration ($TC_{50}$) of Compound 1 (i.e., antroquinonol) and chemotherapy drugs on AsPC-1 cell line was investigated. FIGS. 1 to 7 and Table 2 show the cytotoxicity of Compound 1 and chemotherapy drugs on AsPC-1 cell line. According to these results, it was confirmed that compound 1 and combination treatment of chemotherapy drugs on AsPC-1 cell viability following by drug concentration on Table 3. AsCP-1 cells were individually incubated with compound 1 or each of the drug combinations for 48 h and 72 h. In FIGS. 8 and 9, the viability of AsPC-1 cells incubated with Compound 1, MTT assays of each chemotherapy drug and their combinations for 48 h and 72 h respectively were measured. AsPC-1 cells treated with Compound 1 or chemotherapy drugs alone showed 75% to 80% viability after incubation for 48 h or 72 h. According to these results, the combination therapies of Compound 1 with the selected chemotherapy drugs may have a synergistic effect to control AsPC-1 cell viability. Moreover, these results also indicated a combination of the tested clinical drugs and Compound 1 has a more extreme effect on AsPC-1 human pancreatic cancer cells than the corresponding single drug treatment.

TABLE 2

Effect of anticancer drugs on cytotoxicity at 48 and 72 hours (Antroquinonol = Compound 1)

| Drug | $TC_{50}$ ($\mu M$)[a] | |
|---|---|---|
| | 48 hrs | 72 hrs |
| Antroquinonol | 58.09 | 24.04 |
| Erlotinib | >800 | >800 |
| 5-FU | >800 | >800 |
| Gemcitabine | >800 | >800 |
| Irinotecan | 221.3 | 68.34 |

TABLE 2-continued

Effect of anticancer drugs on cytotoxicity at
48 and 72 hours (Antroquinonol = Compound 1)

| Drug | $TC_{50}$ (μM)[a] | |
|---|---|---|
| | 48 hrs | 72 hrs |
| Oxaliplatin | 654.7 | 57.91 |
| Paclitaxel | 7.054 | 3.719 |

[a]$TC_{50}$: the concentration of the compound at which cell viability was reduced to 50%.

The combinations of Compound 1 with paclitaxel and/or gemcitabine, which have synergistic effect for pancreatic cancer were evaluated. Three pancreatic cancer cell lines, AsPC-1, CaPan-2 and Panc-1 were used to test the combinations through median effect analysis.

TABLE 3

Drugs concentrations used in the combinations
on cytotoxicity of AsPC-1 cells.

| Drug | Conc. (μM) | |
|---|---|---|
| | 48 hrs | 72 hrs |
| Antroquinonol (Compound 1) | 20 | 20 |
| Erlotinib | 100 | 100 |
| 5-FU | 100 | 100 |
| Gemcitabine | 100 | 100 |
| Irinotecan | 200 | 70 |
| Oxaliplatin | 200 | 60 |
| Paclitaxel | 7 | 3 |

Evaluation of the Combination Therapy Effect of
Compound 1 with Chemotherapeutic Drugs,
Gemcitabine and Paclitaxel The median effect analysis of Chou and Talalay (Chou and Talalay, 1984) was used to calculate the CI for each drug combination formula. Therefore, CI value was used to determine if there is a synergy effect between Compound 1 and gemcitabine, and/or paclitaxel in this study. In the AsPC-1, CaPan-2 and Panc-1 cell lines, the two or three compound combinations of Compound 1 with chemotherapy drugs, paclitaxel and gemcitabine, were strongly synergistic (CI<1, FIG. 11) across the entire range of doses (e.g., see FIGS. 10 and 11). These results presented that the exemplary compound (i.e., Compound 1) with a second or third currently used chemotherapeutic drugs strongly inhibit pancreatic cancer growth especially in the three compound combination.

In Vivo Antitumor Activity on AsPC-1
Subcutaneous Xenograft Model

Figure 13:
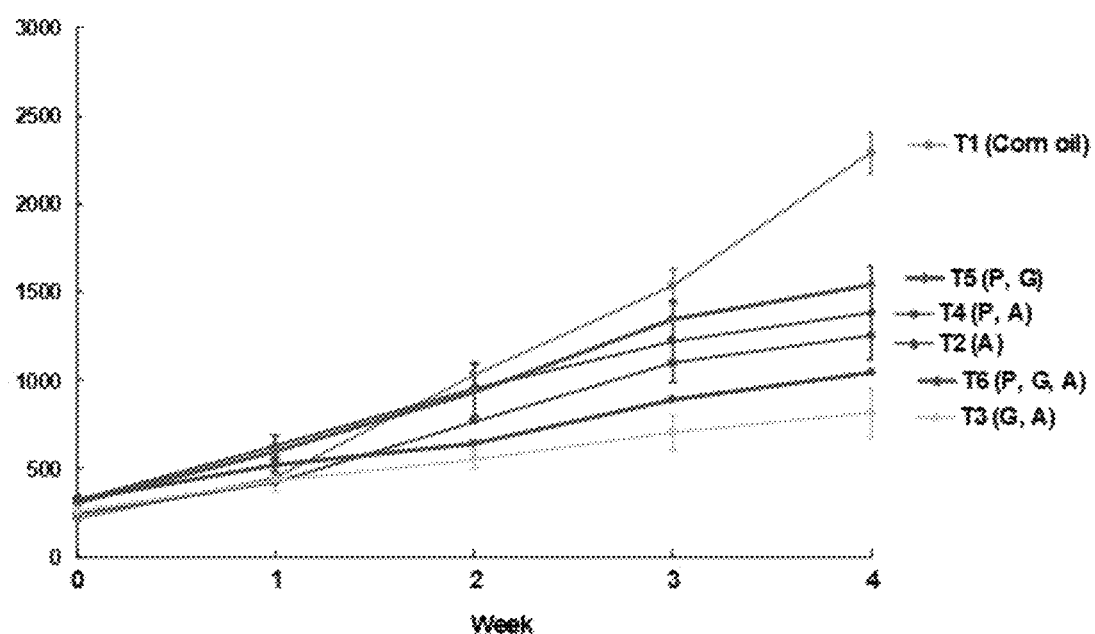
FIG. 13 shows the effect of antitumor activity of Compound 1 plus chemotherapy drugs on AsPC-1 subcutaneous xenograft model. Weekly measurements of tumor size were made and the mean relative tumor volume was plotted as a function of time after the start of treatment. Each point was presented mean of tumor volume.
Figure 14:
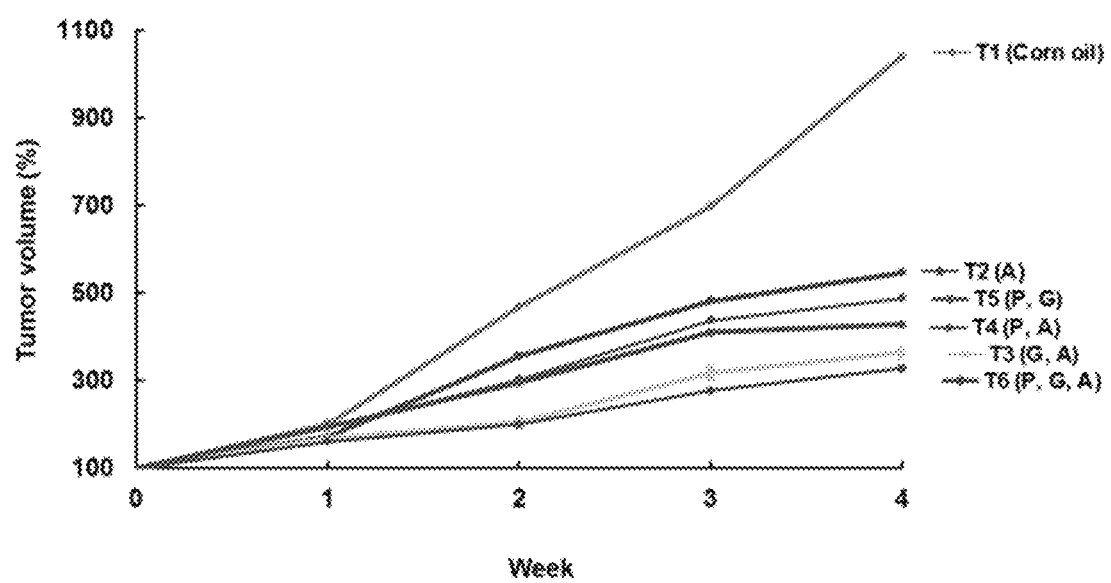
FIG. 14 shows the effect of Compound 1 plus chemotherapy drugs on AsPC-1 subcutaneous xenograft model. Percentage of tumor volume significantly decreased in treatment groups of Compound 1 contained combinations which compared with control group (T1, corn oil).
Figure 15:
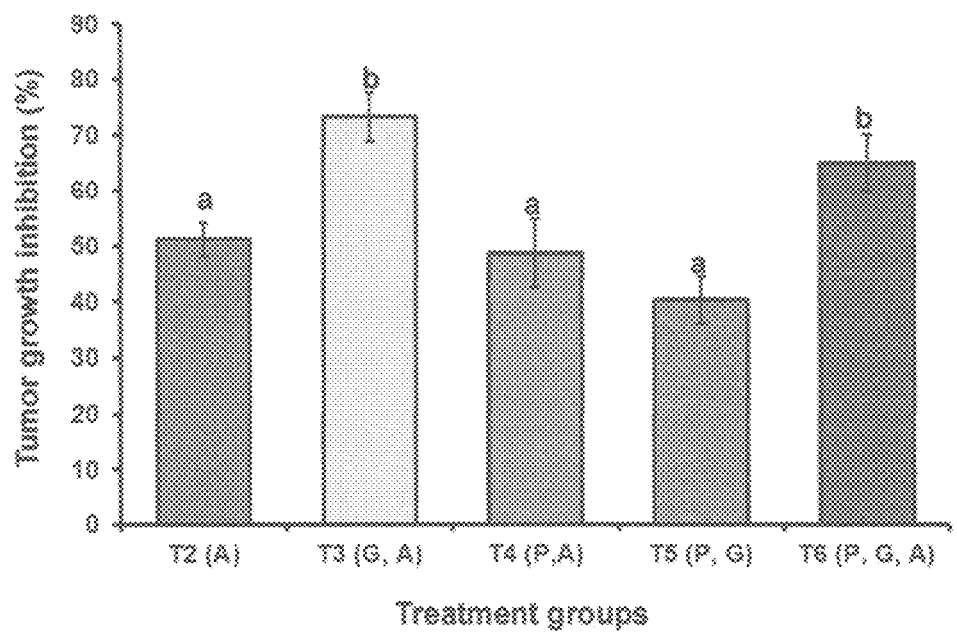
FIG. 15 shows the analysis results of the Tumor Growth Inhibition (TGI) percent of Compound 1 alone or with chemotherapy drugs, paclitaxel and gemcitabine, on the growth of AsPC-1 tumor volume. Each column was presented mean of tumor growth inhibition. Values are means±SEM. Different superscripts denote significant difference ($P<0.05$) between each treatment group.
Figure 16:
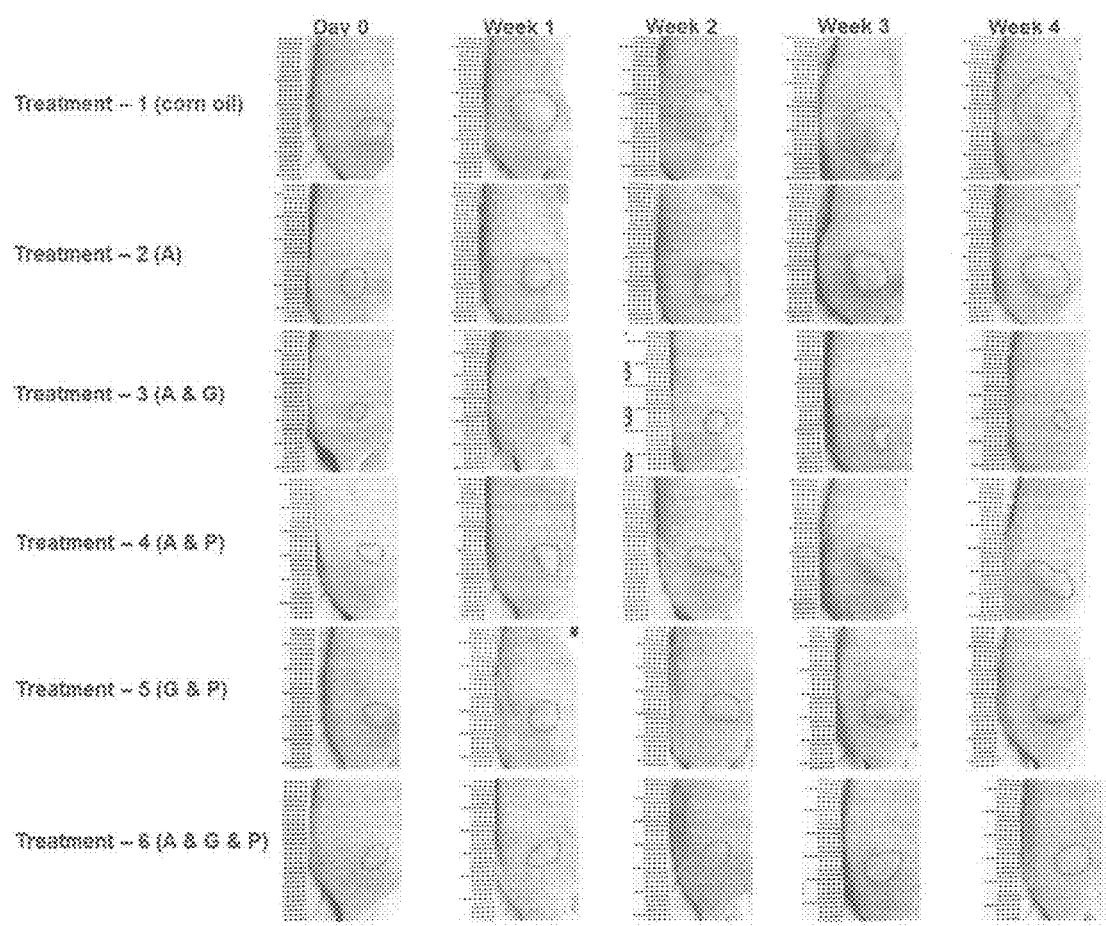
FIG. 16 illustrates the comparison results of representative photo of AsPC-1 pancreatic tumor xenograft before and after treatment with Compound 1 and/or plus chemotherapy drugs, respectively.

The antitumor activity of the combination therapy comprising the exemplary Compound 1 was assessed on AsPC-1 tumor bearing nude mice. AsPC-1 cells were subcutaneously injected 7 days before commencing treatment to the mice (Table 1). These animals then received daily administration of various drug combinations for 28 days. At day 28, all test mice were sacrificed and corresponding tumors were excised for further studies. As shown in FIGS. 13 and 14, at the end of the experiments, the mice treated with the combination of Compound 1 and gemcitabine (T3), or the combination of Compound 1, gemcitabine and paclitaxel (T6), showed a highly significant tumor regression with a slow growing in tumor volume. Mice in the other four treatment groups showed strict tumor growth comparing with groups T3 and T6. The tumor growth inhibition rate increased significantly in the combination of Compound 1 and gemcitabine (T3), or the combination of Compound 1, gemcitabine and paclitaxel (T6) (FIG. 15) compared with the groups (FIG. 16, T2, T4 and T5).

Figure 17:
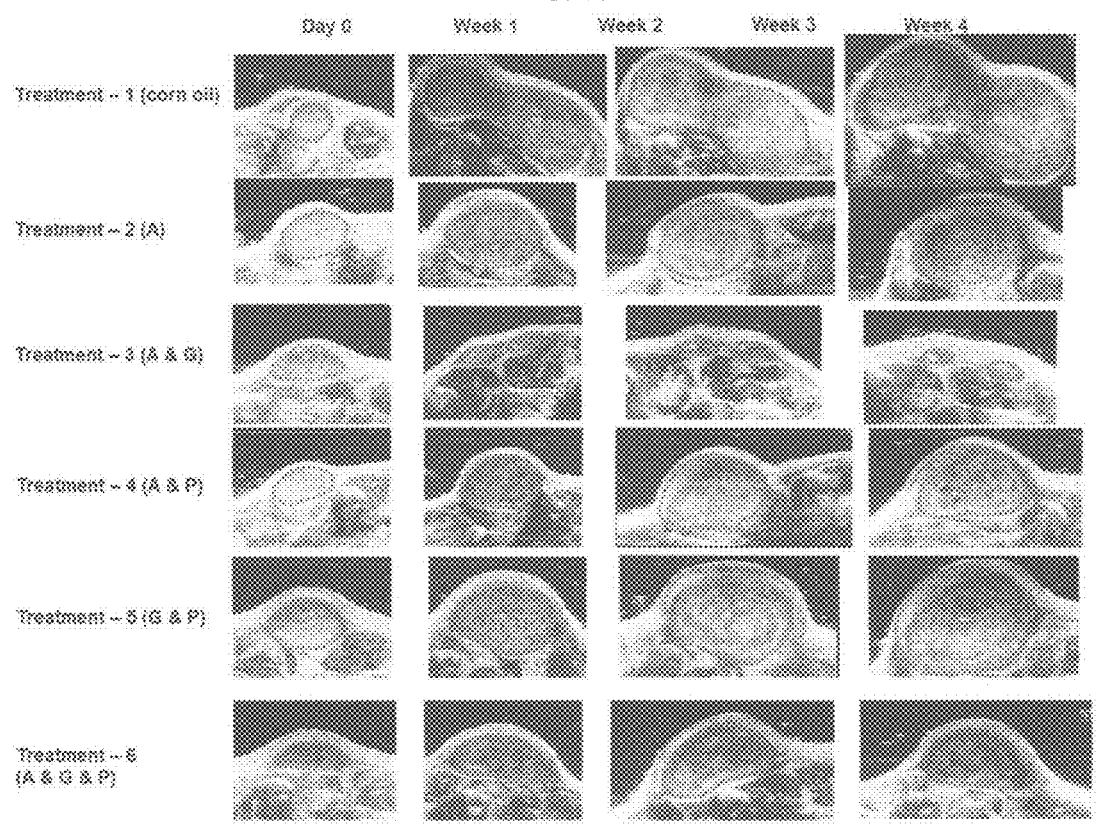
FIG. 17 illustrates the comparison results of representative ultrasound images of AsPC-1 pancreatic tumor xenograft before and after treatment with Compound 1 and/or plus chemotherapy drugs, respectively.
Figure 19:
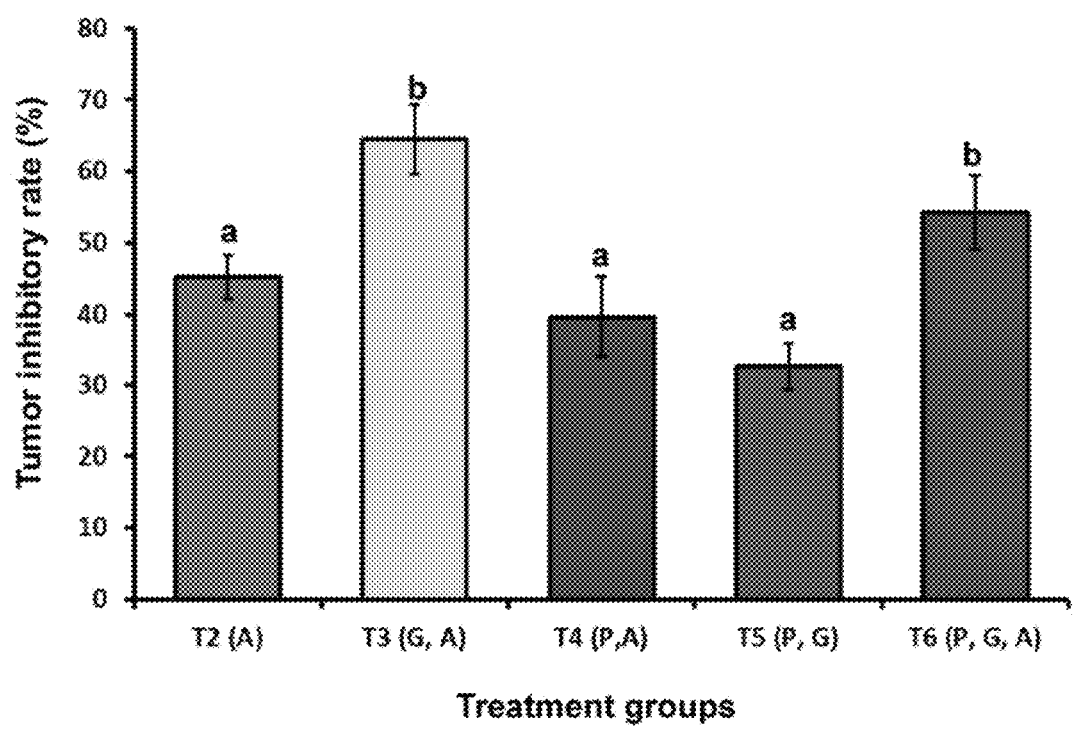
FIG. 19 shows the results of inhibitory effect of Compound 1 alone or with chemotherapy drugs, paclitaxel and gemcitabine, on the growth of AsPC-1 solid tumor. Each column was presented mean of tumor inhibitory rate (TIR). Values are means of TIR±SEM. Different superscripts denote significant difference ($P<0.05$) between each treatment group.

FIG. 17 illustrates the treatment results represented by the ultrasound images of AsPC-1 pancreatic tumor xenograft during the period of treatments. Photographs of the tumors from the sacrificed mice are shown in FIG. 18A. It can be seen that the tumor volumes in mice treated with Compound 1 and gemcitabine are significant smaller than those treated with other combinations. In particular, FIG. 18B shows that the tumor weight in the mice treated with Compound 1 and gemcitabine is much smaller as compared to those in other groups. All of these results demonstrate that the combination therapy described herein does have predominant tumor growth inhibitory efficacy. The tumor inhibitory rate (TRI) in each group was also calculated based on final tumor weights (FIG. 19). Tumor growth was inhibited significantly in the groups of Compound 1 plus gemcitabine (FIG. 19, T3), and Compound 1 plus the other two drugs (FIG. 19, T6).

In order to confirm that therapeutic efficacy of the combination therapy based on the exemplary compound 1 is much better than that of mono-chemotherapy drug, the synergistic effects of the selected drug combinations were evaluated by tumor volume of treatment-to-control ratio (TCR), tumor growth inhibition (TGI) and tumor inhibitory ratio (TIR). In AsPC-1 xenografts, monotherapy of Compound 1 was able to inhibit tumor growth, with treatment-to-control ratios (TCR) of 0.55. The combination of Compound 1 and gemcitabine (Table 4, Ge+Aq) produced a dramatically enhanced antitumor activity compared with the other mono or two-compound combinations treatments (TCR 0.36; Table 4; FIG. 13). In the meantime, the combination with three medicines comprising Compound 1 (Table 4, Px+Ge+Aq) also induced strong antitumor activity compared with either mono or other combination therapies (TCR 0.46; Table 4; FIG. 13). According to those results, Compound 1 in combinations with gemcitabine, or with additional paclitaxel have enhanced antitumor activity, significantly.

Figure 12:
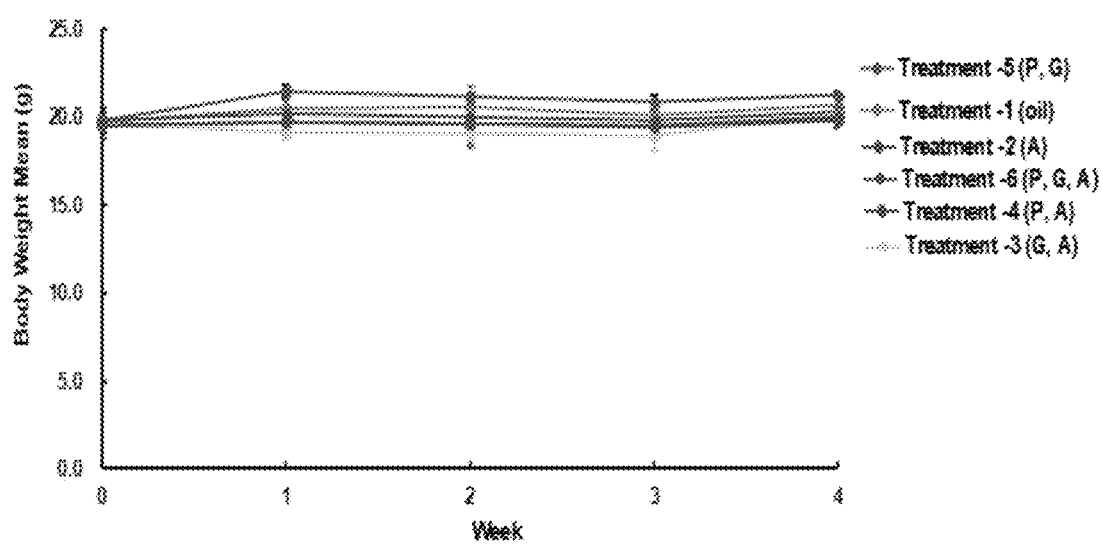
FIG. 12 shows the results of the mice body weight changes during the test of antitumor activity by Compound 1 with chemotherapy drugs on AsPC-1 subcutaneous xenograft model.

In addition, no significant weight loss was observed in the tumor-bearing mice treated with various combinations, indicating negligible side effect of Compound 1 and other two chemotherapy drugs for tumor therapy at the employed doses (FIG. 12). Consistently, Compound 1 and its combinations did not affect number of blood cells except for blood glucose in AsPC-1 xenograft (Table 5.). According to these data, it suggests that Compound 1, and/or its combinations thereof have low safety risk of taking orally.

TABLE 4

Tumor weight of excised tumors at the time of sacrifice from the subcutaneous AsPC-1 pancreatic tumor xenograft-bearing male nude mice after 28 days of treatments.

| | Treatment Groups[#] | | | | | |
|---|---|---|---|---|---|---|
| | T1 | T2 | T3 | T4 | T5 | T6 |
| Tumor weight | 0.42 ± 0.11[a] | 0.21 ± 0.07[b] | 0.11 ± 0.05[b] | 0.22 ± 0.16[b] | 0.31 ± 0.21[b] | 0.24 ± 0.09[b] |

[#]Six treatment groups of the mice administrated corn oil (T1), Compound 1 (T2), combination of Compound 1 and gemcitabine (T3), combination of Compound 1 and paclitaxel (T4), combination of gemcitabine and paclitaxel (T5) and combination of Compound 1, gemcitabine, and paclitaxel (T6).
Tumor weights are means ± SEM. Values in the same row are followed by a different superscript (a-b) are significantly at $P < 0.05$.

TABLE 5

Synergistic antitumor activity by combinations of Compound 1 (Aq), paclitaxel (Px) and gemcitabine (Ge) in AsPC-1 xenograft.

| Xenograft | Treatment | Response, TCR | TGI (%) | TIR (%) |
|---|---|---|---|---|
| AsPC-1 | Control | 1.00 | — | — |
| | Aq | 0.55 | 51 | 45 |
| | Ge + Aq | 0.36 | 73 | 64 |
| | Px + Aq | 0.60 | 49 | 40 |
| | Px + Ge | 0.67 | 40 | 33 |
| | Px + Ge + Aq | 0.46 | 65 | 54 |

Abbreviations: Aq, Compound 1; Px, paclitaxel; Ge, gemcitabine; TCR, tumor volume of treatment-to-control ratios; TGI, volume of tumor growth inhibition; TIR, tumor weight inhibitory ratio.

TABLE 6

Hematological values of each treatment group in AsPC-1 xenograft study.

| Parameter | Unit | T1 (control) | T2 (A) | T3 (G, A) | T4 (P, A) | T5 (P, G) | T6 (P, G, A) | References range of 10-18 week Female ICR mice |
|---|---|---|---|---|---|---|---|---|
| WBC | $10^9$/L | 6.10 ± 0.83 | 7.34 ± 0.71 | 8.92 ± 1.11 | 8.65 ± 0.64 | 7.33 ± 1.46 | 7.65 ± 0.92 | 4.20-8.86 |
| RBC | $10^{12}$/L | 9.16 ± 1.34 | 9.93 ± 1.34 | 9.12 ± 0.94 | 9.05 ± 1.22 | 9.77 ± 1.43 | 9.26 ± 1.57 | 7.99-10.83 |
| HGB | g/dL | 15.5 ± 0.9 | 15.6 ± 1.1 | 15.7 ± 0.4 | 14.6 ± 2.9 | 16.2 ± 1.4 | 16.1 ± 1.9 | 14.3-16.7 |
| HCT | % | 51.2 ± 1.6 | 50.3 ± 1.8 | 52.1 ± 2.1 | 54.9 ± 2.7 | 53.9 ± 2.1 | 55.9 ± 3.3 | 49.0-63.1 |
| MCV | fL | 54.9 ± 1.7 | 53.6 ± 2.3 | 57.6 ± 4.1 | 53.1 ± 1.4 | 56.6 ± 4.3 | 53.1 ± 5.3 | 53.6-65.4 |
| MCH | pg | 15.4 ± 0.5 | 15.3 ± 0.3 | 15.5 ± 0.7 | 16.1 ± 0.6 | 16.1 ± 1.1 | 16.1 ± 1.9 | 15.8-16.8 |

Abbreviations: WBC—white blood count, RBC—red blood cell, HGB—Hemoglobin, HCT—Hematocrit, MCV—mean corpuscular volume, MCH—mean corpuscular hemoglobin. Values are means ± SEM (n = 3 in each treatment group)

As shown in the study results, it is clearly shown the superior unexpected benefits utilizing the compositions comprising the exemplary Compound 1 and the current clinical chemotherapy drugs such as paclitaxel and gemcitabine against pancreatic cancer. Cell viability studies showed that the treatments with such combinations resulted in much higher inhibition activity than either Compound 1 or the other chemotherapy drugs alone, suggesting a synergistic and/or additive effect. Such effect was confirmed by the combinations of compound 1 with gemcitabine alone, and with additional paclitaxel which exhibit significant inhibition of tumor growth on tumor bearing mice.

Example 3. A Phase I Study to Determine the Maximum Tolerated Dose (MTD) and to Evaluate Safety/Tolerability, Pharmacokinetics, Pharmacodynamics and Preliminary Efficacy of Compound 1 in Combination with Nab+Paclitaxel+Gemcitabine in First Line Metastatic Pancreatic Cancer Introduction: In 2011, the multidrug combination of leucovorin, fluorouracil, irinotecan, and oxaliplatin (FOLFIRINOX) was noted to provide an increased median survival of 4.3 months versus gemcitabine; however, given its side effect profile, it is available only to a select group of patients with advanced pancreatic cancer. The patients were randomly assigned to receive FOLFIRINOX or gemcitabine. The median overall survival (OS) was 11.1 months in the FOLFIRINOX group compared with 6.8 months in the gemcitabine group (hazard ratio [HR] for death=0.57; 95% confidence interval [CI], 0.45 to 0.73; p<0.001). Median progression-free survival (PFS) was 6.4 months in the FOLFIRINOX group and 3.3 months in the gemcitabine group (HR for disease progression=0.47; 95% CI, 0.37 to 0.59; p<0.001).

More recently, the gemcitabine plus nab-paclitaxel (the 130-nm albumin-bound nanoparticle formulation of paclitaxel) combination was shown to increase median survival by 1.8 months, with increased OS at 1 and 2 years; adverse effects were reasonable and included cytopenias and peripheral neuropathy. The multi-center, international Phase III MPACT trial included 861 patients with previously untreated metastatic pancreatic adenocarcinoma. The patients were randomly assigned to receive gemcitabine and nab-paclitaxel or gemcitabine monotherapy. The median OS was 8.5 months in the nab-paclitaxel/gemcitabine group compared with 6.7 months in the gemcitabine group (HR for death=0.72; 95% CI, 0.62 to 0.83; p<0.001). Median PFS was 5.5 months in the nab-paclitaxel/gemcitabine group and 3.7 months in the gemcitabine group (HR for disease progression=0.69; 95% CI, 0.58 to 0.82, p<0.001).

The current National Comprehensive Cancer Network recommendations suggest acceptable first-line chemotherapy combinations for patients with good performance status (i.e., Eastern Cooperative Oncology Group (ECOG) performance status (PS) of 0 or 1), based on patient preference and support system available. These combinations include FOLFIRINOX for patients with better/favorable comorbidity profile, or gemcitabine plus nab-paclitaxel for patients with adequate/acceptable comorbidity profile, nab-paclitaxel+gemcitabine, and gemcitabine plus erlotinib. Gemcitabine alone is recommended for patients with ECOG PS 2 or with a comorbidity profile that precludes other regimens; the addition of capecitabine or erlotinib may be offered. The guidelines for choosing an appropriate treatment regimen for patients with metastatic pancreatic cancer thus remain ambiguous, and in the absence of a randomized trial comparing the combination regimens head to head, the most appropriate first-line therapy for these patients remains unclear.

As shown in Example 2, the exemplary compound 1 has shown anti-tumor activity and a low toxicity profile in preclinical in vitro and in vivo animal experiments. In a separate non-clinical study using the orthotopic PANC-1 human pancreatic cancer xenograft model with Compound 1 conducted in 2012, four groups of mice were treated with 30 mg/kg, 60 mg/kg, 90 mg/kg, of Compound 1 and vehicle control, respectively to examine the in vivo therapeutic efficacy of Compound 1. Tumor volumes and tumor weights were measured 10 days after drug treatment (19 days after tumor implantation). Treatment with Compound 1 at 30, 60, and 90 mg/kg produced an effective anti-tumor activity with statistically significant smaller mean tumor volumes and tumor weights in all three dosage levels compared to vehicle control. All three doses of antroquinonol were tolerated well by the tumor bearing mice; there was no severe body weight loss observed during the study.

In the early reported clinical trial studies, Antroquinonol (i.e., Compound 1) at 50, 100, 200, 300, 450, and 600 mg-dose levels, given daily for 4 weeks, was generally safe and well tolerated, as no particular safety concerns or DLTs were identified in this study. The data generated from the safety and pharmacokinetic (PK) profiles in this study could support further studies of antroquinonol in subjects with advanced malignancies to determine the maximum tolerated dose (MTD) and efficacy in given patient populations.

Study Objectives

The primary objectives of this study are: to determine the MTD or maximum feasible dose (MFD) of Compound 1 in combination with nab+paclitaxel+gemcitabine in subjects with metastatic pancreatic cancer. Although Compound 1 has been assessed for a cancer treatment, it is known in the field that many cancer drugs are less effective in treating metastatic cancer.

Cohort expansion: to evaluate the anti-tumor activity of antroquinonol in combination with nab+paclitaxel+gemcitabine in subjects with metastatic pancreatic cancer.

The secondary objectives of this study are:

Dose Escalation:

To evaluate the safety and tolerability of the combination of antroquinonol and nab+paclitaxel+gemcitabine.

To characterize the PK of antroquinonol and nab+paclitaxel+gemcitabine.

To evaluate antroquinonol activity from routine pancreatic cancer monitoring.

To explore the preliminary anti-tumor activity of antroquinonol in combination with nab+paclitaxel+gemcitabine in subjects with metastatic pancreatic cancer.

Cohort expansion: to evaluate the safety and tolerability of MFD of antroquinonol and nab+paclitaxel+gemcitabine combination; to characterize the PK of antroquinonol and nab-paclitaxel-gemcitabine; to evaluate for antroquinonol activity from routine pancreatic cancer monitoring.

Study Endpoints

Primary Endpoints

Dose Escalation:
Occurrence of DLTs in the $1^{st}$ 28-day cycle of treatment. The DLT definition (grading according to NCI Common Terminology Criteria for Adverse Event [CTCAE] v. 4.03):
Non-hematological toxicity of Grade 3 or greater excluding: Grade 3 diarrhea, nausea, or vomiting that resolves within 3 days of onset to Grade 1 or to baseline Grade with appropriate treatment
Grade 4 thrombocytopenia or neutropenia lasting ≥48 hours
≥Grade 3 febrile neutropenia
Grade 3 thrombocytopenia with bleeding
Persisting toxicity of Grade 2 or greater that causes more than a 14 day delay in dose administration.
AEs that are considered by the Investigator to be related to the underlying disease condition, concomitant medication, or to new unrelated medical events or treatment will not be defined as a DLT.
Cohort Expansion:
Primary endpoint: To evaluate the anti-tumor activity of antroquinonol in combination with nab+paclitaxel+gemcitabine in subjects with metastatic pancreatic cancer.
Secondary Endpoints:
Safety: Safety will be evaluated using AEs, physical examinations, laboratory findings (including clinical chemistry, hematology, and urinalysis), vital signs (including blood pressure and pulse), and electrocardiograms (ECGs).
Efficacy: Objective response rate (ORR), duration of response (DoR), disease control rate (DCR), and PFS using Investigator assessments according to RECIST 1.1 (assessments to occur every 8 weeks), OS.
Pharmacokinetics: Plasma concentration of antroquinonol and nab+paclitaxel+gemcitabine combination and PK parameters will be evaluated.
Biomarkers: To evaluate antroquinonol activity from routine pancreatic cancer monitoring.

Investigation Plan

Overall Study Design and Plan Description

This is a single-arm, open-label, multi-center Phase I study of Compound 1 in combination with nab-paclitaxel and gemcitabine in first line treatment naïve subjects with Stage IV metastatic pancreatic carcinoma.

The first part of the study will follow a 3+3 dose escalation design to determine the MTD or MFD (based on PK and capsules strength) of antroquinonol in combination with standard dose regimen of nab-paclitaxel and gemcitabine. Two dose levels of antroquinonol given TID are planned based on dose escalation data and capsules strengths. The final number of subjects will be based on the number of dose levels investigated and DLTs occurrence. Up to 12 subjects may be treated in this part of the study. A Safety Monitoring Committee (SMC) will be set up for this study to review DLTs and overall safety data and judge the relevance of events to the dose escalation scheme.

After MTD/MFD determination, enrollment will continue at a fixed dose of antroquinonol (MTD or MFD). A maximum of 40 evaluable subjects is planned in this cohort expansion part of the trial.

Investigational Product, Dosage, and Mode of Administration

Escalating doses of Compound 1 (200 to 300 mg) per oral, TID administration, until unacceptable toxicity or disease progression, and in the absence of discontinuation criteria.

125 mg/m² nab-paclitaxel and 1000 mg/m² gemcitabine via intravenous (IV) infusion, both administered on Days 1, 8, and 15 of each 28-day cycle (ie, 1 cycle=weekly for 3 weeks, then 1 week off) until unacceptable toxicity or disease progression.

DLT Definition and Evaluation

Dose limiting toxicity is defined as the occurrence of any of the toxicities outlined below occurring during the DLT evaluation period that are determined to be related or possibly related to investigational medicinal products (IMP) combination. The DLT evaluation period will be the first 28-day treatment cycle. Toxicity grading will be determined using NCI CTCAE version 4.03. Dose limiting toxicities will be defined as:
Non-hematological toxicity of Grade 3 or greater excluding:
Grade 3 diarrhea, nausea, or vomiting that resolves within 3 days of onset to Grade 1 or to baseline Grade with appropriate treatment.
Grade 4 thrombocytopenia or neutropenia lasting 248 hours
2 Grade 3 febrile neutropenia
Grade 3 thrombocytopenia with bleeding
Persisting toxicity of Grade 2 or greater that causes more than a 14 day delay in dose administration.
AEs that are considered by the Investigator to be related to the underlying disease condition, concomitant medication, or to new unrelated medical events or treatment will not be defined as a DLT.

Selection of Study Population

Inclusion Criteria: To be eligible to participate in the study, subjects must meet the following criteria:
1. Male and female subjects ≥18 years or older.
2. Histologically or cytologically confirmed metastatic ductal adenocarcinoma of the pancreas, measurable according to the RECIST 1.1.
3. Metastatic disease had to have been diagnosed within 6 weeks before randomization.
4. Treatment-naïve subjects with metastatic pancreatic ductal adenocarcinoma who have received no previous systemic therapy (except adjuvant or neoadjuvant therapy if progression occurred >6 months from last treatment or surgery, respectively, and no prior nab-paclitaxel).
5. Adequate hematologic, hepatic, and renal function, including: Hemoglobin≥9 g/dL
Absolute neutrophil count≥1500/mm³
Platelet count≥100 000/mm³
Total bilirubin≤1.5×upper limit of normal (ULN) except subjects with documented Gilbert's syndrome (>3×ULN)
Alanine aminotransferase (ALT) and aspartate aminotransferase (AST)≤2.5×ULN; for subjects with hepatic metastases, ALT and AST≤5×ULN
Albumin≥3 mg/dL
Serum creatinine≤1.5 mg/dL or calculated creatinine clearance≥50 mL/min as determined by the Cockcroft-Gault equation
ECOG of 0 or 1.
6. For women of childbearing potential, a negative serum pregnancy test result at Screening and on Day 1.
7. Willing to use two medically accepted and effective methods of contraception from the list below during the study (both men and women as appropriate) and for 3 months after the last dose of study drug:
Established use of oral, injected, or implanted hormonal methods of contraception
Placement of an intrauterine device or intrauterine system
Barrier methods of contraception: Condom or Occlusive cap (diaphrag or cervical/vault caps) with spermicidal foam/gel/film/cream/suppository
Male sterilization (with the appropriate postvasectomy documentation of the absence of sperm in the ejaculate)
True abstinence: When this is in line with the preferred and usual lifestyle of the subject.
8. Signed ICF.
9. Life expectancy≥12 weeks.

Exclusion Criteria: Subjects who meet any of the following criteria will not be eligible to participate in the study:
1. Islet-cell neoplasms or locally advanced disease.
2. Chemo-, hormone-, or immunotherapy or investigational drug within 4 weeks or five half-lives of the date of first administration of study drug (whichever is shorter) and/or persistence of toxicities of prior anticancer therapies which are deemed to be clinically relevant.
3. Treatment with any drug(s) known to be a strong inhibitor or inducer of cytochrome P450 (CYP) 2C19, CYP3A4, CYP2C8, and CYP2E1 within 14 days of the date of first administration of study drug and during study treatment.
4. Other malignancies diagnosed within the past five years (other than curatively treated cervical cancer in situ, nonmelanoma skin cancer, superficial bladder tumors Ta [noninvasive tumor] and TIS [carcinoma in situ], or nonmetastatic prostate cancer Stage 1 to 2, which has been previously treated with surgery or radiation therapy, and serum prostate-specific antigen is within normal limits [test performed within the past 12 months prior to the date of first administration of study drug]).
5. Subjects with any serious active infection (ie, requiring an intravenous antibiotic, antifungal, or antiviral agent).
6. Subjects with known human immunodeficiency virus, active hepatitis B, or active hepatitis C.
7. Subjects who have any other life-threatening illness or organ system dysfunction, which in the opinion of the Investigator, would either compromise subject safety or interfere with the evaluation of the safety of the study drug.
8. Known or suspected substance abuse or alcohol abuse.
9. Uncontrolled intercurrent illness, including, but not limited to, ongoing or active infection, symptomatic congestive heart failure, uncontrolled hypertension, unstable angina pectoris, cardiac arrhythmia, interstitial lung disease, or psychiatric illness/social situations that would limit compliance with study requirement, substantially increase risk of incurring AEs from study treatment, or compromise the ability of the subject to give written informed consent.
10. Inability to swallow oral medications or a recent acute gastrointestinal disorder with diarrhea, eg, Crohn's disease, malabsorption, or CTCAE Grade>2 diarrhea of any etiology at baseline.
11. Female subjects who are pregnant or breastfeeding, or male or female subjects of reproductive potential who are not employing an effective method of birth contraception.

Withdrawal of Subjects: Subjects may withdraw their consent to participate in the study and investigators may withdraw subjects at any time without prejudice. Subjects will be withdrawn from the study or study treatment if any of the conditions set below has occurred:
1. Documented disease progression according to the response criteria.
2. Unacceptable toxicity.
3. Subject decides to withdraw his/her informed consent.
4. Investigator considers that the subject is no longer physically and/or psychologically able to remain in the study.

Replacement Procedures: During the dose escalation phase, a subject who does not experience DLTs in the first cycle and who meets any of the following should be replaced with new subject:
All planned trial treatment dosing are not completed in the first 28-day cycle.
All planned trial treatment dosing are completed with/without delay; however, 90% of the planned total dose of either drug is not administered in the first cycle.

Guidance to Investigators on When to End Study Treatment Regimen: Subjects may withdraw their consent to participate in the study and investigators may withdraw subjects at any time. Subjects will be withdrawn from the study or study treatment if any of the following conditions are met:
1. Lost to follow-up.
2. Any AE or medical condition that the Investigator or Sponsor determines may jeopardize the subject's safety if he or she continues in the study.
3. Pregnancy or intent to become pregnant.
4. Subject noncompliance that, in the opinion of the Investigator or Sponsor, warrants withdrawal from study medication (eg, refusal to adhere to scheduled visits).
5. Initiation of alternative anti-cancer therapy, including another investigational agent.
6. Confirmed progressive disease and Investigator determination that the subject is no longer benefiting from study treatment.
7. The Sponsor terminates the study. Reasons for terminating the study may include, but are not limited to, the following: the incidence or severity of AEs in this or other studies indicates a potential health hazard to subjects; subject enrollment is unsatisfactory.

Follow-up of Subjects Prematurely Discontinued From the Study Treatment Regimen or Withdrawn From Study:
All subjects will attend a safety follow-up visit 28 days after receiving the last administration of study treatments. Subjects who discontinue investigational product prematurely will be asked to return to the clinic for an early termination visit and may undergo follow-up assessments. The primary reason for premature investigational product discontinuation should be documented on the appropriate electronic case report form (eCRF).

Treatment of Subjects

Treatments Administered: Compound 1 will be administered in 200- to 300-mg doses (planned dose levels), TID, given in 100 mg capsules (resulting a daily dosage of 600 mg to 900 mg). Additional dose levels may be investigated as determined by the study SMC. The study drug will be filled in #2 capsules (100 mg) and then packed in a light-protected polyethylene bottle and closed with a piece of polyethylene cap liner fitted in the cap for each dispensation at Visit 1 (Day 0), 3 (Day 28), 4 (Day 42), 5 (Day 56), and 6 (Day 84), and subsequent visits for subjects entering the Extension Phase. The study drug will be labeled in accordance with country-specific requirements. Several doses of antroquinonol are planned for the first dose escalation part of the trial. Dose escalation will follow a 3+3 design based on DLT occurrence. The starting dose of antroquinonol will be 200 mg TID, which is the dose currently investigated in the ongoing Phase II single-agent trial in NSCLC. If there are no DLTs or ≤1/6 subjects with DLT, the dose will be escalated to 300 mg TID. One dose (MTD or MFD) will be investigated in the cohort expansion part of the trial.

Subjects will receive antroquinonol as long as they are continuing to show clinical benefit, as judged by the Investigator, and in the absence of discontinuation criteria. Antroquinonol should be taken every 8 hours approximately 15 minutes after a meal or light snack and not within ±1 hour of drinking an ethanol-containing beverage, eg, an alcoholic drink. Subjects who forget or are unable to take a dose at the scheduled time should be instructed to take the dose as soon as possible. If they do not remember or are unable to take the dose prior to the next scheduled dose, they should take the scheduled dose and the missed dose will not be made up. The date and time of each study drug administration should be recorded in the subject diary.

The recommended dose of nab-paclitaxel in combination with gemcitabine is 125 mg/m$^2$ via IV infusion over 30 minutes on Days 1, 8, and 15 of each 28-day cycle. The concurrent recommended dose (RD) of gemcitabine is 1000 mg/m$^2$ via IV infusion over 30 minutes immediately after the completion of nab-paclitaxel administration on Days 1, 8, and 15 of each 28-day cycle. Treatment with nab-paclitaxel+gemcitabine will continue until unacceptable toxicity or disease progression. Per clinical practice and local regulation, in case of subject toxicity, the Day 15 treatment administration can be omitted. In this case, the start of the subsequent cycle will begin early, on Day 22 of the first cycle administration (except for Cycle 1, the DLT period). The tumor assessment schedule will not be altered (ie, assessments will continue to be every 8 weeks).

Selection and Timing of Dose for Each Subject: In the dose escalation part of the study, subjects will be enrolled and treated sequentially following a 3+3 dose escalation design. In the cohort expansion part, subjects will be enrolled and treated in parallel.

Efficacy and Safety Variables

Efficacy Assessments: The RECIST 1.1 criteria will be used to assess subject response to treatment by determining ORR, DoR, DCR, PFS, PFS 3 months, and PFS 6 months. The RECIST 1.1 guidelines for measurable, non-measurable, target, and non-target lesions and the objective tumor response criteria (complete response [CR], partial response

[PR], stable disease [SD], or progressive disease) are presented based on revised response evaluation criteria in solid tumors guidelines Version 1.1—adaptation from original publication with addition of supplementary explanations. The OS, OS 6 months, and OS 12 months will also be evaluated.

The baseline assessments should be performed no more than 28 days before start of study treatment and ideally should be performed as close as possible to the start of study treatment. Efficacy for all subjects will be assessed by objective tumor assessments every 8 weeks for the first 12 months and every 12 weeks thereafter until confirmed objective disease progression. If an unscheduled assessment is performed and the subject has not progressed, every attempt should be made to perform the subsequent assessments at his or her scheduled visits.

A confirmatory scan is required following the initial demonstration of progressive disease. The confirmatory scan should occur preferably at the next scheduled visit and no earlier than 4 weeks after the initial assessment of progressive disease in the absence of clinically significant deterioration. Treatment will continue between the initial assessment of progression and confirmation for progression. If a subject discontinues treatment (and/or receives a subsequent anti-cancer therapy) prior to progression, then the subject should still continue to be followed until confirmed objective disease progression.

Objective tumor response (CR or PR) should be confirmed preferably at the next scheduled visit and not less than 4 weeks after the visit when the response was first observed.

Following confirmed progression, subjects should continue to be followed up for survival every 2 months (8 weeks). In addition, all subjects will be contacted in the week following data cutoff to confirm survival status.

Safety Assessments: Safety will be monitored throughout the study for all subjects. The analysis of the safety data will be performed using the Safety Analysis Set.

Adverse Events:

Definitions: The term "adverse event," as used by the Sponsor, is synonymous with the term "adverse experience," which is used by the FDA.

An AE is any untoward, undesired, unplanned clinical event in the form of signs, symptoms, disease, or laboratory or physiological observations occurring in a human being participating in a clinical study with a Sponsor test article, regardless of causal relationship. This includes the following:

Any clinically significant worsening of a pre-existing condition

Note: Emergence of a new pathogen associated with a clinical event during therapy at a site other than the initial site of infection will be considered to be an AE.

Any recurrence of a pre-existing condition

An AE occurring from overdose of a Sponsor study drug whether accidental or intentional (ie, a dose higher than that prescribed by a health care professional for clinical reasons)

An AE occurring from abuse of a Sponsor study drug (ie, use for nonclinical reasons)

An AE that has been associated with the discontinuation of the use of a Sponsor study drug.

Note: A procedure is not an AE, but the reason for a procedure may be an AE.

A pre-existing condition is a clinical condition (including a condition being treated) that is diagnosed before the subject signs the ICF and that is documented as part of the subject's medical history.

The questions concerning whether the condition existed before the start of the active phase of the study and whether it has increased in severity and/or frequency will be used to determine whether an event is a TEAE. An AE is considered to be treatment-emergent if (1) it is not present when the active phase of the study begins and is not a chronic condition that is part of the subject's medical history, or (2) it is present at the start of the active phase of the study or as part of the subject's medical history, but the severity or frequency increases during the active phase. The active phase of the study begins at the time of the first dose of the study drug. The active phase of the study ends at the follow-up visit.

Reporting of Adverse Events: At each visit the Investigator, or delegate, will determine whether or not any AEs have occurred. The subject will be questioned in a general way and no specific symptoms will be suggested. If any AEs have occurred, they will be recorded in the AE section of the eCRF and in the subject's medical records. If known, the diagnosis should be recorded, in preference to listing the individual signs and symptoms.

Adverse event reporting begins from the time of informed consent and ends 30 days after the last dose of IMP.

Assessment of Severity: The AE severity grading scale for the NCI CTCAE (version 4.03) will be used for assessing AE severity. For AEs that are not specifically listed in the NCI CTCAE, the following definitions will be used:

Grade 1: Mild; asymptomatic or mild symptoms; clinical or diagnostic observations only; or intervention not indicated.

Grade 2: Moderate; minimal, local, or noninvasive intervention indicated; or limiting age-appropriate instrumental activities of daily living.

Grade 3: Severe or medically significant, but not immediately life-threatening; hospitalization or prolongation of hospitalization indicated; disabling; or limiting self-care activities of daily living.

Grade 4: Life-threatening consequences or urgent intervention indicated.

Grade 5: Death related to AE.

Relationship to Study Treatment: The Investigator will make a determination of the relationship of the AE to the study drug using a four-category system according to the following guidelines:

Unrelated: Clinical event with an incompatible time relationship to drug administration, and that could be explained by underlying disease or other drugs or chemicals or is incontrovertibly not related to the study drug.

Unlikely: Clinical event whose time relationship to drug administration makes a causal connection improbable, but that could plausibly be explained by underlying disease or other drugs or chemicals.

Possible: Clinical event with a reasonable time relationship to study drug administration, but that could also be explained by concurrent disease or other drugs or chemicals.

Definite: Clinical event with plausible time relationship to study drug administration, and that cannot be explained by concurrent disease or other drugs or chemicals.

Follow-up of Adverse Events: It is important for the investigators to take information of underlying diseases, concomitant drugs, and temporal relationship of the onset of the event to the time of dosing the study drug, and re-challenging outcomes, into account when making a causal relation decision. It is the Investigators' responsibility to follow proactively the outcome of each AE until resolution or stabilization of the condition, alternative treatment for pancreatic cancer is started, 6 months after last dose of study drug, or loss to follow-up, whichever occurs first. In the event of serious or study drug-related toxicities, the subject will be followed until resolution or stabilization. Safety follow-up data may be collected by telephone contact every 3 months after the End of Study Visit.

Serious Adverse Events: A serious adverse event (SAE) is any AE occurring at any dose that meets 1 or more of the following criteria:
Results in death
Is life-threatening (see below)
Requires subject hospitalization or prolongation of an existing hospitalization (see below)
Results in a persistent or significant disability or incapacity (see below)
Results in a congenital anomaly or birth defect
Results in an important medical event (see below).

Additionally, important medical events that may not result in death, be life-threatening, or require hospitalization may be considered SAEs when, based on appropriate medical judgment, they may jeopardize the subject and may require medical or surgical intervention to prevent one of the outcomes listed above. Examples of such events include allergic bronchospasm requiring intensive treatment in an emergency room or at home, blood dyscrasias or convulsions that do not require hospitalization, or development of drug dependency or drug abuse.

A life-threatening AE is any AE that places the subject at immediate risk of death from the event as it occurred. A life-threatening event does not include an event that might have caused death had it occurred in a more severe form but that did not create an immediate risk of death as it actually occurred. For example, drug-induced hepatitis that resolved without evidence of hepatic failure would not be considered life-threatening, even though drug-induced hepatitis of a more severe nature can be fatal. Hospitalization is to be considered only as an overnight admission.

Hospitalization or prolongation of a hospitalization is a criterion for considering an AE to be serious. In the absence of an AE, the participating Investigator should not report hospitalization or prolongation of hospitalization.

In addition, a hospitalization planned before the start of the study for a pre-existing condition that has not worsened does not constitute an SAE (eg, elective hospitalization for a total knee replacement due to a pre-existing condition of osteoarthritis of the knee that has not worsened during the study).

Disability is defined as a substantial disruption in a person's ability to conduct normal life functions. If there is any doubt as to whether a case constitutes an AE or SAE based on the information available, the case should be treated as an SAE.

Alternatively, medical and scientific judgment should be exercised in deciding whether a case is serious in those situations where important medical events may not be immediately life-threatening or result in death, hospitalization, disability, or incapacity. These include events that may jeopardize the subject or may require medical intervention to prevent one or more outcomes listed in the definition of serious.

Pharmacokinetic Analysis

Noncompartmental PK analyses will be performed on individual plasma concentration data. The PK analyses will be performed using commercial software such as Phoenix™ WinNonlin® Version 6.4 or higher (Certara USA, Inc.). Maximum plasma concentration ($C_{max}$), trough (predose) concentration ($C_{trough}$), and the time of $C_{max}$ ($T_{max}$) will be taken directly from the observed data. The area under the plasma concentration-time curve ($AUC_\tau$) will be calculated using the linear trapezoidal rule. The PK parameters will be listed for each individual and summarized by treatment group using descriptive statistics (sample size [N], arithmetic mean, standard deviation, coefficient of variation [CV %], median, minimum, maximum, and geometric mean). Individual concentration data will be listed and summarized by treatment group with descriptive statistics (N, arithmetic mean, standard deviation, median, minimum, maximum, geometric mean, and CV %). Mean and individual plasma concentration-time profiles will be presented graphically on both linear and semilogarithmic scales.

Actual dose administration times and sample collection times will be used for the analyses as recorded on the case report form. Plasma concentrations below the lower limit of quantification will be set to zero for the analysis. Pharmacokinetic parameter estimates will be three or four significant figures for presentation. No attempt will made to estimate missing data. Other parameters and data handling procedures may be added as appropriate. Only subjects who are given active antroquinonol and have evaluable concentration-time profiles will be included in the analysis. All statistical analyses will use nonrounded parameter estimates.

A population PK (PopPK) model development and analysis may be performed using mixed-effects methods. Dosing, sampling, demographic, and laboratory data from each subject will be assembled into a database suitable for a population analysis. A nonlinear mixed-effects model will be developed using NONMEM (Globomax, Ellicot City, Md.). Various structural models will be evaluated as indicated by the data. Covariate effects (age, gender, race, body size, smoking history, etc.) will be evaluated and incorporated into the model using univariate or multivariate approaches. Once the optimal model has been established, it will be validated using standard methods, such as visual predictive checks and bootstrap analyses.

The potential exposure-exposure/concentration relationships could be evaluated based on the post hoc estimates of antroquinonol exposure (ie, model predicted $C_{max}$, $C_{trough}$, and $AUC_\tau$) from the above PopPK model or the concentration observations.

Statistical Methods

General Consideration: For study reporting purposes the following aspects will be considered:
Descriptive statistics and graphical presentations will be the main analysis tools.
Subject disposition will be reported for each dose level using the All Subjects Set for both Phases of studies, and subject profiles will be presented for the dose escalation phase of the study only.
For all analyses, results, and graphical representation of individual subject data will be presented by dose level. The dose level to which a subject was assigned at the first treatment will be indicated on all outputs.
Descriptive statistics and graphical representations will be used to summarize the data for each dose level. The following summary statistics will be used to summarize the trial data per dose level based on their nature, unless otherwise specified:

Continuous variables: number of nonmissing observations (N), mean, standard deviation, median, minimum, and maximum; 95% CI will be presented where appropriate.

Categorical variables: frequencies and percentages.

Details of the statistical analysis will be presented in the Statistical Analysis Plan.

Efficacy Analysis

Primary Outcome Measures:

Dose escalation phase: The number and proportion of subjects experiencing DTLs in each dose level during Cycle 1 will be assessed on the DLT Analysis Set.

Cohort expansion phase: Descriptive summary of subjects with best overall response in each category (CR, PR, SD, and progressive disease); the objective response rate (CR+PR); the disease control rate (CR+PR+SD [SD of ≥16 weeks]) with 95% CIs according to RECIST 1.1 will be performed on Efficacy Analysis Set.

Criteria in Solid Tumors (RECIST) version 1.1 will be performed for median OS time and PFS time with 95% CI will be evaluated using Kaplan-Meier methods on Full Analysis Set. The OS is defined as the time from first dose of study drug to subject death. The PFS is defined as the time from first dose of study drug to the start of disease progression or subject death, whichever occurred first.

Analysis of Secondary Outcome Measures: Data of secondary endpoints will be listed by dose level, subject, and visit (if applicable). Secondary endpoints will be descriptive analyzed by dose level in the relevant analysis set.

Safety and Tolerability Analysis: The number and proportion of subjects experiencing TEAEs; drug exposure; clinically significant changes in laboratory parameters, vital signs, physical examinations, weight, ECOG performance status, ECGs, and/or pulse oximetry, judged to be related to the trial medication; and number and reasons of deaths will be summarized.

Safety evaluation will include incidence of AEs (or TEAEs), laboratory test results, vital signs, ECG results, and physical examination findings. All summaries of safety data will be based on the Safety Analysis Set. No formal statistical analysis of the safety data will be performed.

Summary tables will be presented for all Adverse Effects (AEs) by dose level and Medical Dictionary for Regulatory Activities SOC and preferred term where applicable. The incidence and type of the following AEs will be analyzed.

An AE will be considered as "treatment-emergent" if it occurred after the first study treatment or if it occurred before the first study treatment and worsened thereafter.

The TEAE summary tables will include counts of subjects. Therefore, if a subject experiences more than one episode of a particular AE, the subject will be counted only once for that event. If a subject has more than one AE that is coded to the same preferred term, the subject will be counted only once for that preferred term. Similarly, if a subject has more than one AE within an SOC, the subject will be counted only once in that SOC.

All deaths and deaths within 30 days of the last dose of study treatment as well as reasons for death will be tabulated by dose level. Drug exposure will be summarized by dose level.

Clinically significant laboratory test variables will be summarized by dose level and visit (if applicable) using descriptive statistics (number of subjects, mean, standard deviation, minimum, maximum, as well as mean change from baseline, standard deviation for mean and standard error for mean change, minimum, median, maximum, and number and percent of subjects within specified categories). Shift tables (ie, cross-tabulations of below the lower limit of the normal range, within the limits of the normal range and above the upper limit of the normal range at baseline versus scheduled visits) will be presented by laboratory test (if applicable). Laboratory tests with categorical results that cannot be analyzed by change from baseline or shift table analysis will not be included in these summaries, but will be listed. Data obtained from laboratory tests not required by the protocol will not be summarized, but will be listed.

Descriptive statistics of vital signs, weight and ECG results at each visit will be presented by treatment group. Physical examination findings will be listed for each subject. The overall response rate and the DCR will be estimated along with 95% CIs calculated using the method of Clopper and Pearson by dose level.

Pharmacokinetic Analysis

Pharmacokinetic Sampling: The PK sampling will be performed on Day 0 and Day 28 in all subjects enrolled in the first stage at the following time points:

Day 0: (Approximately 5 mL per sample, 60 mL in total) 30 minutes prior to and 0.5, 1, 2, 3, 4, 6, and 8 hours after the first dose.

Day 28: (Approximately 5 mL per sample, 60 mL in total) immediately before and 0.5, 1, 2, 3, 4, 6, and 8 hours after the first dose on Day 28.

Sparse PK sampling will be performed on Days 28, 42, and 56 in all subjects enrolled in Stage 2. At least two samples will be collected on each occasion, one of which will be a trough concentration (30 minutes prior to the first dose on Days 28, 42, and 56 and approximately 8 hours after the last dose on the prior day). At least one sample per subject will be timed to coincide with the peak concentration (3 hours after the first dose). The remainder may be taken at any time during the dosing interval.

Each blood sample will be analyzed for antroquinonol plasma concentration to determine PK parameters after administration of antroquinonol using a fully validated bioanalytical method (a copy of the analytical method validation report and bioanalytical report will be included in the clinical study report).

Pharmacokinetic Sampling Procedures

Blood Samples: Samples of venous blood will be obtained in 5 mL sodium heparin Vacutainer® tubes at the prescheduled sample times. Immediately after collection the tube will be gently inverted 8 to 10 times to mix the anticoagulant with the blood sample. All samples will be processed and placed into a freezer within one (1) hour after collection. The plasma fraction will be separated by placing the collection tube into a refrigerated centrifuge (4° C.) for 10 minutes at 3000 rpm. The plasma fraction will be withdrawn by pipette and divided into two polypropylene freezing tubes (with each tube receiving approximately equal aliquots). All sample collection and freezing tubes will be clearly labeled with the subject number, the study period, and the collection time. Labels will be fixed to freezing tubes in a manner that will prevent the label from becoming detached after freezing. All plasma samples will be placed into a freezer at −70° C. within 1 hour after collection.

Analytical Methodology: The concentration of study drug will be determined from the plasma samples using a validated analytical method. Details of the method validation and sample analysis will be included in the final clinical study report.

Preliminary Results:

The preliminary results from the patients with 600 mg daily dosage shows that the patient tumor size (mm) reduced after the completion of the 3$^{rd}$ cycle (8 weeks treatment). One patient's tumor size reduced 7.6% from 91 mm to 84 mm, and the other patient's tumor size reduced 22% from 50 mm to 39 mm. The preliminary tumor size reduction further supports the superior unexpected benefits of the invention compositions comprising the exemplary Compound 1 and the current clinical chemotherapy drugs such as paclitaxel and gemcitabine against pancreatic cancer as shown in the animal study.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for treating pancreatic cancer in a subject comprising administering the subject in need thereof a composition comprising

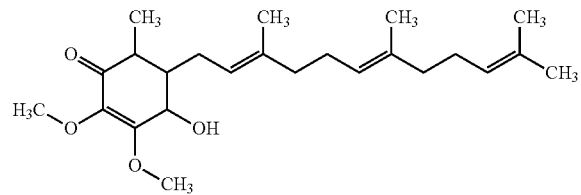 [SMILES: COC1=C(OC)C(O)C(C/C=C(\C)CC/C=C(\C)CCC=C(C)C)C(C)C1=O]

and one or more anti-cancer agents;

or a pharmaceutically acceptable salt, or solvate thereof, wherein the one or more anti-cancer agents is erlotinib, 5-FU, oxaliplatin, irinotecan, gemcitabine, paclitaxel, or a combination thereof.

2. The method of claim 1, wherein said compound, or a pharmaceutically acceptable salt, or solvate thereof, is administered orally, parenterally, intravenously or by injection.

3. The method of claim 1, wherein said method further comprises administering an immunotherapy agent.

4. A method for the treatment of a patient whose pancreatic cancer is resistant, refractory or non-responsive to gemcitabine, paclitaxel, or a combination thereof, comprising administering the patient in need thereof with

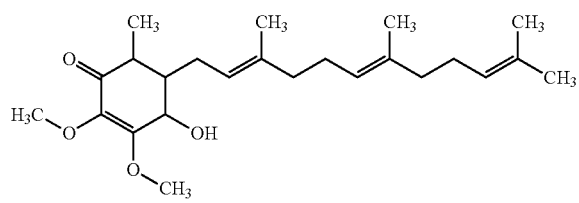 [SMILES: COC1=C(OC)C(O)C(C/C=C(\C)CC/C=C(\C)CCC=C(C)C)C(C)C1=O]

or a pharmaceutically acceptable salt, or solvate thereof.

5. The method of claim 4, wherein said compound, or a pharmaceutically acceptable salt, or solvate thereof, is administered orally, parenterally, intravenously or by injection.

6. The method of claim 4 wherein said method further comprises administering an immunotherapy agent.

7. The method of claim 1, wherein the one or more anti-cancer agents is gemcitabine, paclitaxel, or a combination thereof.

* * * * *